United States Patent
Cao et al.

(10) Patent No.: US 10,538,757 B2
(45) Date of Patent: Jan. 21, 2020

(54) NANOZYMES, METHODS OF MAKING NANOZYMES, AND METHODS OF USING NANOZYMES

(71) Applicant: University of Florida Research Foundation, Inc., Gainesville, FL (US)

(72) Inventors: Yunwei Charles Cao, Gainesville, FL (US); Chen Liu, New Brunswick, NJ (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/042,935

(22) Filed: Feb. 12, 2016

(65) Prior Publication Data

US 2016/0215279 A1 Jul. 28, 2016

Related U.S. Application Data

(63) Continuation-in-part of application No. PCT/US2014/050803, filed on Aug. 13, 2014.

(60) Provisional application No. 61/865,650, filed on Aug. 14, 2013.

(51) Int. Cl.
*C12N 9/96* (2006.01)
*C12N 11/14* (2006.01)
*A61K 38/43* (2006.01)
*C12N 11/08* (2006.01)

(52) U.S. Cl.
CPC .............. *C12N 11/14* (2013.01); *A61K 38/43* (2013.01); *C12N 11/08* (2013.01)

(58) Field of Classification Search
None
See application file for complete search history.

(56) References Cited

U.S. PATENT DOCUMENTS

| | | |
|---|---|---|
| 6,479,146 B1 | 11/2002 | Caruso |
| 6,677,122 B2 | 1/2004 | Mirkin et al. |
| 7,550,441 B2 | 6/2009 | Farokhzad et al. |
| 7,829,140 B1 | 11/2010 | Zhong |
| 2003/0219384 A1 | 11/2003 | Donath |
| 2004/0052729 A1 | 3/2004 | Penades et al. |
| 2005/0058603 A1 | 3/2005 | Gao |
| 2007/0009417 A1 | 1/2007 | Wong |
| 2008/0279946 A1 | 11/2008 | Hainfeld |
| 2009/0053169 A1 | 2/2009 | Castillo et al. |
| 2013/0034532 A1 | 2/2013 | Cao |

FOREIGN PATENT DOCUMENTS

| | | |
|---|---|---|
| CA | 2648099 A1 | 9/2008 |
| EP | 1847600 A1 | 10/2007 |
| JP | 20010031308 | 11/2001 |
| JP | 2002526383 | 8/2002 |
| JP | 2007289167 | 11/2007 |
| JP | 2008500364 | 1/2008 |
| JP | 2009534309 | 9/2009 |
| WO | 2004045494 | 6/2004 |
| WO | 2006044716 A2 | 4/2006 |
| WO | 2008105773 | 9/2008 |
| WO | 2009077599 A2 | 6/2009 |
| WO | 2010009087 | 1/2010 |
| WO | 2010014895 A2 | 2/2010 |
| WO | 2010033913 A1 | 3/2010 |
| WO | 2010117957 A2 | 10/2010 |

OTHER PUBLICATIONS

Lynch, et al., Gas-Bubble Effects on the Formation of Colloidal Iron Oxide Nanocrystals, J. Am. Chem. Soc. 2011, 133, 12664-12674.
Wang, et al., Nanoparticle-based Artificial RNA Silencing Machinery for Antiviral Therapy, Proceedings of the National Academy of Sciences, 2012, 109, 12387-12392.
Peer D, et al. (2007) Nanocarriers as an emerging platform for cancer therapy. Nat Nanotechnol 2:751-760.
Giljohann DA, et al. (2010) Gold nanoparticles for biology and medicine. Angew Chem Int Edit 49:3280-3294.
Alivisatos P (2004) The use of nanocrystals in biological detection. Nat Biotechnol 22:47-52.
Medintz IL, Uyeda HT, Goldman ER, Mattoussi H (2005) Quantum dot bioconjugates for imaging, labelling and sensing. Nat Mater 4:435-446.
Nederberg F, et al. (2011) Biodegradable nanostructures with selective lysis of microbial membranes. Nat Chem 3:409-414.
Qian XM, et al. (2008) In vivo tumor targeting and spectroscopic detection with surface-enhanced Raman nanoparticle tags. Nat Biotechnol 26:83-90.
Wu W, Li AD (2007) Optically switchable nanoparticles for biological imaging. Nanomedicine (Lond) 2:523-531.
Graham D, Thompson DG, Smith WE, Faulds K (2008) Control of enhanced Raman scattering using a DNA-based assembly process of dye-coded nanoparticles. Nat Nanotechnol 3:548-551.
Cho EC, Zhang Q, Xia YN (2011) The effect of sedimentation and diffusion on cellular uptake of gold nanoparticles. Nat Nanotechnol 6:385-391.
Kim B, et al. (2010) Tuning payload delivery in tumour cylindroids using gold nanoparticles. Nat Nanotechnol 5:465-472.
Brigger I, Dubernet C, Couvreur P (2002) Nanoparticles in cancer therapy and diagnosis. Adv Drug Deliv Rev 54:631-651.
Yezhelyev MV, Qi LF, O'Regan RM, Nie S, Gao XH (2008) Proton-sponge coated quantum dots for siRNA delivery and intracellular imaging. J Am Chem Soc 130:9006-9012.
Khaled A, Guo SC, Li F, Guo PX (2005) Controllable self-assembly of nanoparticles for specific delivery of multiple therapeutic molecules to cancer cells using RNA nanotechnology. Nano Lett 5:1797-1808.

(Continued)

*Primary Examiner* — Hope A Robinson
(74) *Attorney, Agent, or Firm* — Thomas|Horstemeyer, LLP

(57) ABSTRACT

Embodiments of the present disclosure provide for nanozymes that can include a therapeutic agent, methods of making nanozymes, methods of using nanozymes, and the like. In some embodiments, the nanozymes can include a shell that can surround a hollow core that can be configured to receive a compound and the shell can include a recognition moiety and an enzyme.

23 Claims, 12 Drawing Sheets

Specification includes a Sequence Listing.

(56) References Cited

OTHER PUBLICATIONS

Shu D, Shu Y, Haque F, Abdelmawla S, Guo PX (2011) Thermodynamically stable RNA three-way junction for constructing multifunctional nanoparticles for delivery of therapeutics. Nat Nanotechnol 6:658-667.
Moazed D (2009) Small RNAs in transcriptional gene silencing and genome defence. Nature 457:413-420.
Park SJ, Taton TA, Mirkin CA (2002) Array-based electrical detection of DNA with nanoparticle probes. Science 295:1503-1506.
Pan Y, et al. (2007) Size-dependent cytotoxicity of gold nanoparticles. Small 3:1941-1949.
Rosi NL, et al. (2006) Oligonucleotide-modified gold nanoparticles for intracellular gene regulation. Science 312:1027-1030.
Raines, Ronald T. (1998) Ribonuclease A. Chem. Rev. 98: 1045-1065.
Bendayan M(1989) "The Enzyme-Gold Cytochemical Approach: A Review"in Colloidal Gold Principles, Methods, and Applications, edMA Hayat (Academic Press, San Diego), vol. 2, pp. 117-147.
Tsai WL, Chung RT (2010) Viral hepatocarcinogenesis. Oncogene 29:2309-2324.
Lanford RE, et al. (2010) Therapeutic silencing of microRNA-122 in primates with chronic hepatitis C virus infection. Science 327:198-201.
Ploss A, Rice CM (2009) Towards a small animal model for hepatitis C. EMBO Rep 10:1220-1227.
McMullan LK, et al. (2007) Evidence for a functional RNA element in the hepatitis C virus core gene. Proc Natl Acad Sci USA 104:2879-2884.
Yokota T, et al. (2003) Inhibition of intracellular hepatitis C virus replication by synthetic and vector-derived small interfering RNAs. EMBO Rep 4:602-608.
Demers LM, Mucic RC, Reynolds RA, Mirkin CA, Letsinger RL (2000) Fluorescence-based method for the determination of surface coverage and hybridization efficiency of thiol-capped oligonucleotides bound to gold nanoparticles. Abstr Pap Am Chem Soc 219:U870-U870.
Lazarides AA, Schatz GC (2000) DNA-linked metal nanosphere materials: Structural basis for the optical properties. J Phys Chem B 104:460-467.
Cerritelli SM, Crouch RJ (2009) Ribonuclease H: The enzymes in eukaryotes. FEBS J 276:1494-1505.
Kelly BM, Yu CZ, Chang PL (1989) Presence of a lysosomal-enzyme, arylsulfatase-a, in the prelysosome-endosome compartments of human cultured fibroblasts. Eur J Cell Biol 48:71-78.
Randall G, Grakoui A, Rice CM (2003) Clearance of replicating hepatitis C virus replicon RNAs in cell culture by small interfering RNAs. Proc Natl Acad Sci USA 100:235-240.
Kobe B, Deisenhofer J (1996) Mechanism of ribonuclease inhibition by ribonuclease inhibitor protein based on the crystal structure of its complex with ribonuclease A. J Mol Biol 264:1028-1043.
Marques JT, Williams BRG (2005) Activation of the mammalian immune system by siRNAs. Nat Biotechnol 23:1399-1405.
Zhu HZ, et al. (2003) Gene expression associated with interferon alfa antiviral activity in an HCV replicon cell line. Hepatology 37:1180-1188.
Kanda T, Steele R, Ray R, Ray RB (2007) Small interfering RNA targeted to hepatitis C virus 5' nontranslated region exerts potent antiviral effect. J Virol 81:669-676.
Lindenbach BD, Rice CM (2005) Unravelling hepatitis C virus replication from genome to function. Nature 436:933-938.
Changeux JP, Edelstein SJ (2005) Allosteric mechanisms of signal transduction. Science 308:1424-1428.
Cutler, J.I.; Zhang, K.; Zheng, D.; Auyeung, E.; Prigodich, A.E.; Mirkin, C.A. "Polyvalent Nucleic Acid Nanostructures,", J. Am. Chem. Soc. 2011, 133, 9254-9257.
Farazi, P.A. & DePinho, R.A. Hepatocellular carcinoma pathogenesis: from genes to environment. Nat Rev Cancer 6, 674-87 (2006).
El-Serag, H.B. Hepatocellular carcinoma. N Engl J Med 365, 1118-27 (2011).
Scagliotti, G.V., Novello, S. & von Pawel, J. The emerging role of MET/HGF inhibitors in oncology. Cancer treatment reviews 39, 793-801 (2013).
Venepalli, N.K. & Goff, L. Targeting the HGF-cMET Axis in Hepatocellular Carcinoma. Int J Hepatol 2013, 1-11 (2013).
Yap, T.A. & de Bono, J.S. Targeting the HGF/c-Met axis: state of play. Mol Cancer Ther 9, 1077-9 (2010).
Cecchi, F., Rabe, D.C. & Bottaro, D.P. Targeting the HGF/Met signalling pathway in cancer. Eur J Cancer 46, 1260-70 (2010).
Dudas G, Rambaut A. Phylogenetic Analysis of Guinea 2014 EBOV Ebolavirus Outbreak. PLoS Curr 2014;6.
Team WHOER. Ebola virus disease in West Africa—the first 9 months of the epidemic and forward projections. N Engl J Med 2014;371:1481-95.
Hoenen T, Safronetz D, Groseth A, et al. Virology. Mutation rate and genotype variation of Ebola virus from Mali case sequences. Science 2015;348:117-9.
Rodriguez LL, De Roo A, Guimard Y, et al. Persistence and genetic stability of Ebola virus during the outbreak in Kikwit, Democratic Republic of the Congo, 1995. J Infect Dis 1999;179 Suppl 1:S170-6.
Blight KJ, McKeating JA, Rice CM. Highly permissive cell lines for subgenomic and genomic hepatitis C virus RNA replication. J Virol 2002;76:13001-14.
Date T, Miyamoto M, Kato T, et al. An infectious and selectable full-length replicon system with hepatitis C virus JFH-1 strain. Hepatol Res 2007;37:433-43.
Yang D, Zuo C, Wang X, et al. Complete replication of hepatitis B virus and hepatitis C virus in a newly developed hepatoma cell line. Proc Natl Acad Sci U S A 2014;111:E1264-73.
Palese P, Zheng H, Engelhardt OG, et al. Negative-strand RNA viruses: genetic engineering and applications. Proc Natl Acad Sci U S A 1996; 93:11354-8.
International Search Report and Written Opinion for PCT/US2014/050803 dated Dec. 16, 2014.
Xin Yu, et al. Carbon Nanotube Amplification Strategies for Highly Sensitive Immunodetection of Cancer Biomarkers, Journal of the American Chem Society, 128:34, Aug. 1, 2006, pp. 11199-11205.
Londono, I., et al. Brief Review on Progresses in Enzyme-Gold Cytochemistry, Scanning Microscopy Supplement, Scanning Microscopy International, Chicago, IL, US, vol. 3, Jan. 1, 1989, pp. 7-14.
Rosi, Nathaniel L., et al., Oligonucleotide-modified gold nanoparticles for intracellular gene regulation, Science, American Association for the Adv of Science, US, 312:5776, May 19, 2006, pp. 1027-1030.
Ke, R., et al., Tandem conjunction of enzyme and antibody on silica nanoparticle for enzyme immunoassay, Analytical Biochemistry, Academic Press Inc., New York, 406:1, Nov. 1, 2010, pp. 8-13.
Reukov, Vladimir, et al., Proteins conjugated to poly(butyl cyanoacrylate) nanoparticles as potential neuroprotective agents, Biotechnology and Bioengineering, 108:2, Oct. 26, 2010, pp. 243-252.
Soon Hye Yang, Nanoparticle-based Cellular Machinery for the Degradation of Specific RNA and Protein, Aug. 1, 2011, pp. 1-58.
Supplemental Search Report for European Application EP 11772525, based on PCT/US1132980. Dated Mar. 29, 2016.
Youle, et al., RNase inhibition of human immunodeficiency virus infection of H9 cells; Proc. Natl. Acad. Sci. USA vol. 91, pp. 6012-6016, Jun. 1994, Medical Sciences; 6 pages.
Cover letter and Office Action for Japanese patent application 2013-506223, Applicant: University of Florida Research Foundation, Inc.; dated Jun. 16, 2015; 14 Pages; Japanese Patent Office.
Suri, et al., RNase: A Novel Enzyme For Treatment of Cancers, The Internet Journal of Oncology, vol. 5, pp. 1-8.
Grunweller, et al., Locked Nucleic Acid Oligonucleotides, Biodrugs, 2007, vol. 21, pp. 235-243.
Li, et al., Nanosize delivery as an emerging platform for cancer therapy, Cancer Biology and Therapy, 2008, vol. 7, pp. 1860-1862.
Jia, et al., Catalytic Behaviors of Enzymes Attached to Nanoparticles: The Effect of Particle Mobility. Biotechnology and Bioengineering, Sep. 11, 2003, 84:4, pp. 406-414.
Liu, et al., Highly sensitive protein detection using enzyme-labeled gold nanoparticle probes. Analyst 135.2 (2010): 327-331.

(56) References Cited

OTHER PUBLICATIONS

International Preliminary Report on Patentability for PCT/US2011/032980 dated Nov. 1, 2012.
International Search Report for PCT/US2011/032980 dated Jan. 4, 2012.
Lee, et al., Enhanced Bioaffinity Sensing Using Surface Plasmons, Surface Enzyme Reactions, Nanoparticles and Diffraction Gratings, Analyst 2008, 133, pp. 596-601.
Zhang, et al., Recent Advances in Nanotechnology Applied to Biosensors, Sensors, 2009, vol. 9, pp. 1033-1053.
Kalaugher, Gold Nanoparticles and Bio-Bar Codes Bring Sensitive DNA Detection; nanotechweb.org, May 6, 2004.
Walter, et al., A unified view of ligand-protected gold clusters as superatom complexes, PNAS, Jul. 8, 2008, vol. 105, No. 27. pp. 9157-9162.

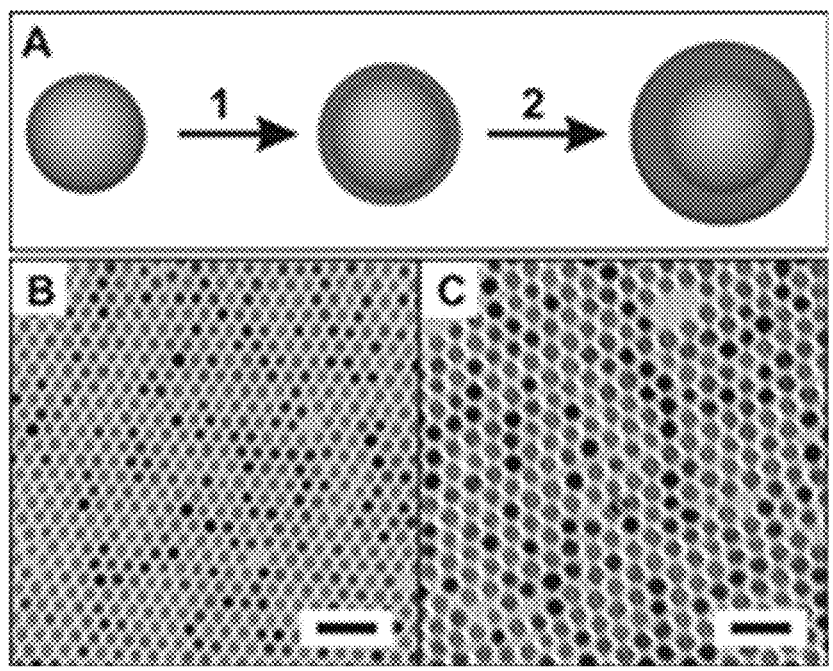
FIG. 1A
FIG. 1B   FIG. 1C
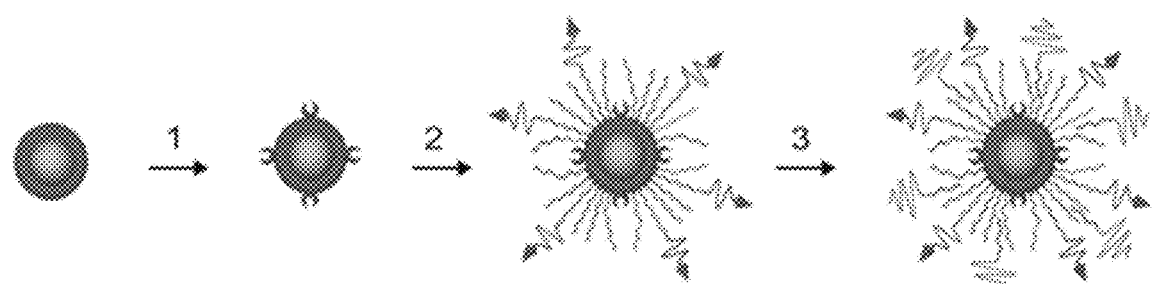
FIG. 2

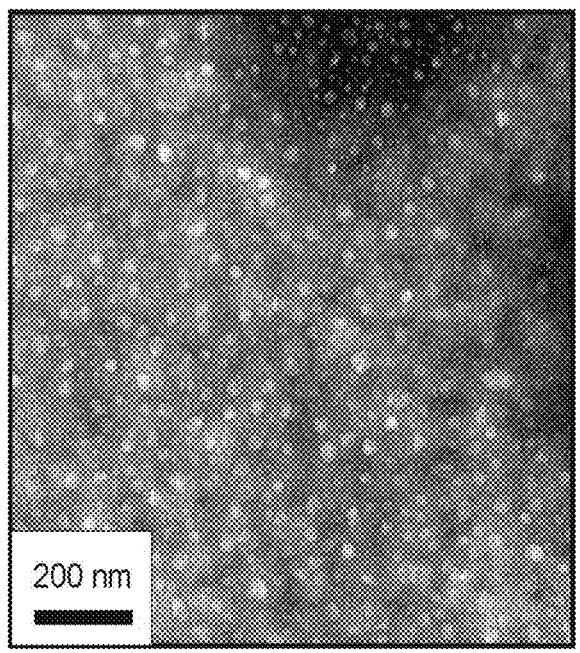 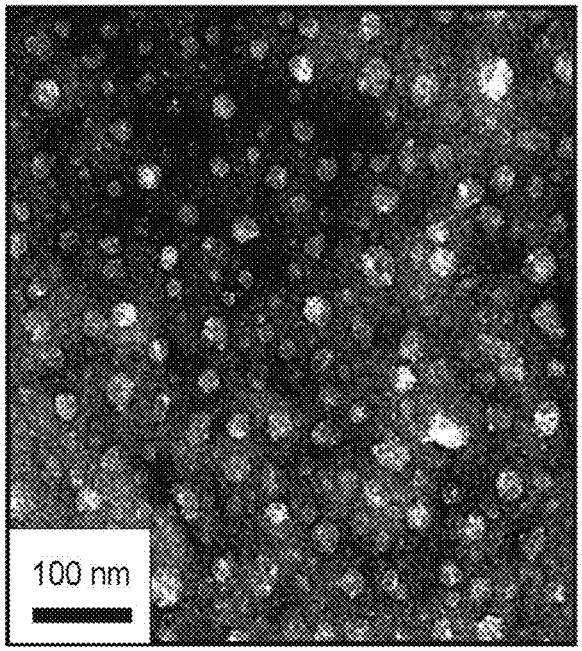
FIG. 6A  FIG. 6B
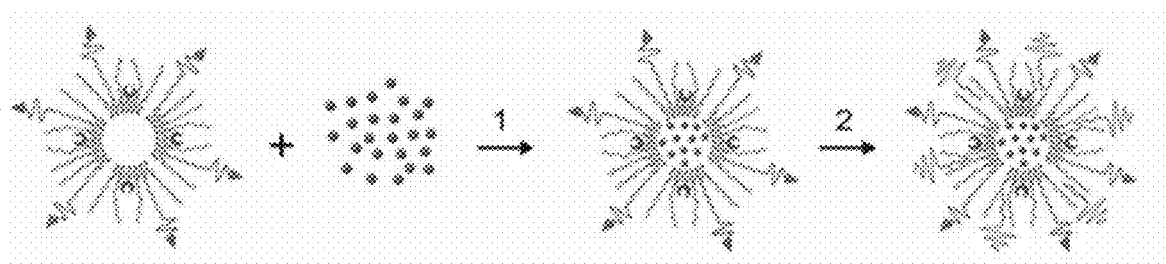
FIG. 7

EBOV cGP region (+)

6446  6463
5'-GUA-UGA-UCG-ACU-UGC-UUC-CAC-AGU-3'  SEQ ID NO: 16

Probe 1  S-AAA-AAA-AAA-ACT-AGC-TGA-ACG-AAG-GTG  SEQ ID NO: 18

EBOV cGP region (-)

6509  6526
5'-CAG-AAA-GUC-GUU-CCU-CGG-UAG-UUC-3'  SEQ ID NO: 17

Probe 2  S-AAA-AAA-AAA-TTT-CAG-CAA-GGA-GCC-ATC  SEQ ID NO: 19

FIG. 14B

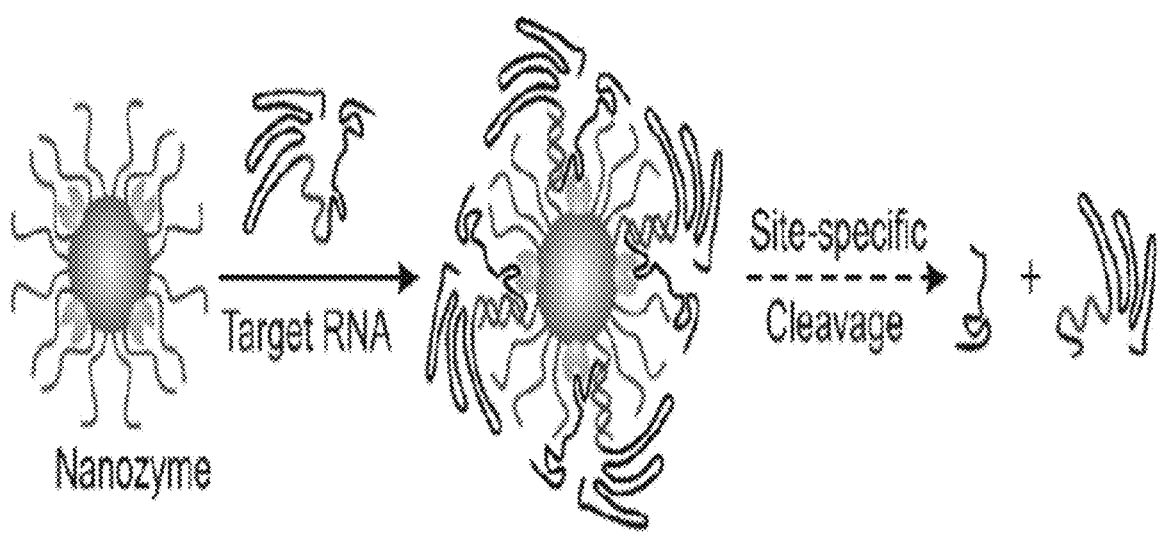
FIG. 14C
FIG. 15A            FIG. 15B
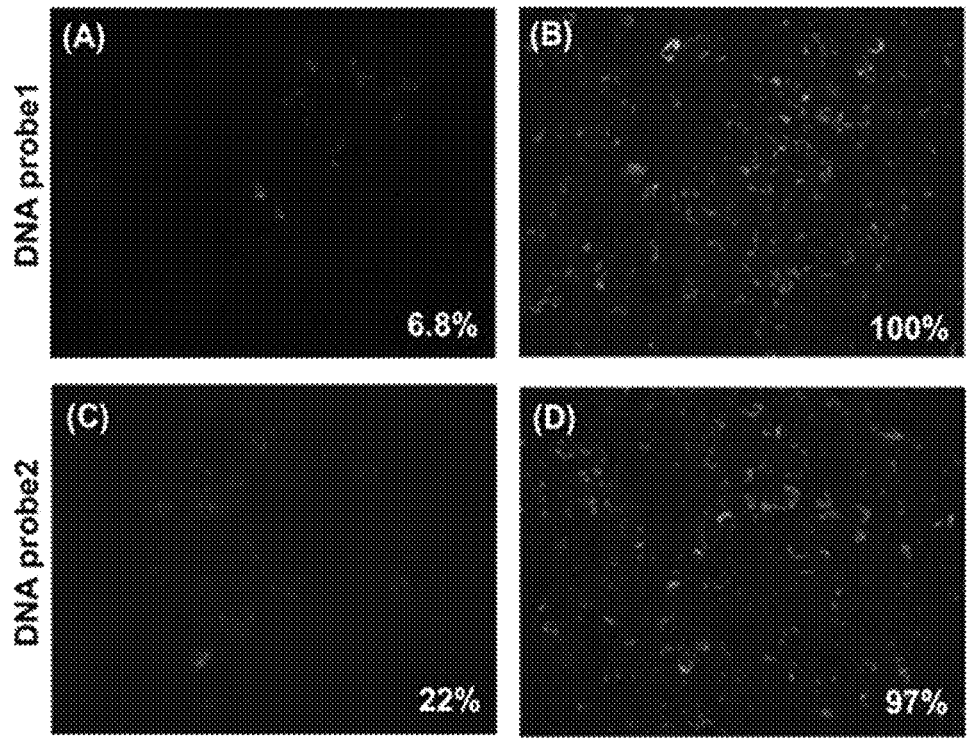
FIG. 15C            FIG. 15D

NANOZYMES, METHODS OF MAKING NANOZYMES, AND METHODS OF USING NANOZYMES

CROSS-REFERENCE TO RELATED APPLICATION

This application is a Continuation-in-Part of International Application entitled "NANOZYMES, METHODS OF MAKING NANOZYMES, AND METHODS OF USING NANOZYMES" having the serial number PCT/US14/50803, filed on Aug. 13, 2014, which is incorporated herein by reference as if expressed in its entirety. In addition, application having serial number PCT/US14/50803 claims priority to U.S. Provisional Application entitled "NANOZYMES, METHODS OF MAKING NANOZYMES, AND METHODS OF USING NANOZYMES" having Ser. No. 61/865,650, filed on Aug. 14, 2013, which is incorporated herein by reference as if expressed in its entirety.

SEQUENCE LISTING

This application contains a sequence listing filed in electronic form as an ASCII.txt file entitled 222109_1110_ST25.txt, created on Feb. 12, 2016. The content of the sequence listing is incorporated herein in its entirety.

BACKGROUND

To date, enzymes have been widely used in medicine. Most enzymes are used extracellularly for topical applications (e.g., collagenase), removal of toxic substances (e.g., rhodonase), and disorders within blood circulation system (e.g., urokinase). In addition, enzymes have a major potential application in treatment of cancer, e.g., asparagenase in the treatment of lymphocytic leukemia. However, enzyme applications in medicine are limited by and suffer from many limitations such as enzyme target specificity, enzyme stability against proteinase, and enzyme activity in the presence of its inhibitors in physiological environments, such as inside cytoplasmic matrix. Thus, there is a need to overcome limitation associated with enzyme.

SUMMARY

Embodiments of the present disclosure include nanozymes having a nanoparticle, hollow nanozymes, hollow nanozymes including a therapeutic agent, methods of making nanozymes, methods of using nanozymes, and the like.

One exemplary embodiment of a nanozyme, among others, includes: a nanoparticle, an enzyme, and a recognition moiety, where each of the enzyme and the recognition moiety are attached to the surface of the nanoparticle, wherein the nanoparticle is an Au nanoparticle.

One exemplary embodiment of a nanozyme, among others, includes: a core/shell nanoparticle, an enzyme, and a recognition moiety, each of the enzyme and the recognition moiety, are attached to the surface of the nanoparticle, wherein the nanoparticle is a $Fe_3O_4$/Au core/shell nanoparticle. In an embodiment, the enzyme does not react with the recognition moiety and an optional protecting moiety attached to the core/shell nanoparticle. In an embodiment, the nanozyme can include a protecting moiety, wherein the protecting moiety is attached to the core/shell nanoparticle. In an embodiment, the nanozyme can include a therapeutic agent. In an embodiment, the $Fe_3O_4$ of the core/shell nanoparticle can function as an imaging agent. In an embodiment, the gold of the core/shell nanoparticle can function as a photothermal therapy agent. In an embodiment, the nanozyme can include an inter- and intra-cellular traffic guiding moiety attached to the core/shell nanoparticle. In an embodiment, the nanozyme can include an allosterically functional moiety, attached to the core/shell nanoparticle.

One exemplary embodiment of a hollow nanozyme, among others, includes: a polymer layer surrounding a hollow core, wherein the polymer layer includes an enzyme, a recognition moiety, and a protecting moiety, where each of the enzyme, the recognition moiety, and the protecting moiety, are on the outside surface of the polymer layer, wherein the hollow core has a diameter of about 1 to 5000 nm. In an embodiment, the polymer layer includes a plurality of pores through the polymer layer. In an embodiment, the hollow nanozyme can include a therapeutic agent disposed in the hollow core.

One exemplary embodiment of a method of forming a hollow nanozyme, among others, includes: providing a nanozyme having a nanoparticle core, wherein an enzyme, a recognition moiety, and a protecting moiety, are attached to the surface of the nanoparticle core; forming a polymer layer from a portion of one or more of the following: the enzyme, the recognition moiety, and the protecting moiety, wherein the polymer layer is formed at one end of one or more of the following: the enzyme, the recognition moiety, and the protecting moiety, so that the polymer layer surrounds the nanoparticle core; and removing the nanoparticle core leaving the polymer layer surrounding a hollow core.

One exemplary embodiment of a method of loading a hollow nanozyme, among others, includes: providing a hollow nanozyme, wherein the hollow nanozyme includes a polymer layer surrounding a hollow core, wherein the polymer layer includes an enzyme and a recognition moiety, where each of the enzyme and the recognition moiety, are on the outside surface of the polymer layer, wherein the polymer layer includes a plurality of pores, wherein the hollow core has a diameter of about 1 to 5000 nm; disposing a therapeutic agent into the hollow nanozyme through the pores of the polymer layer; and disposing a protecting moiety onto the polymer layer, wherein the protecting moiety substantially blocks the pores so the therapeutic agent does not exit the pores.

One exemplary embodiment of a method of administering a therapeutic agent, among others, includes: administering a hollow nanozyme to a subject having a condition, wherein the hollow nanozyme includes a polymer layer surrounding a hollow core, wherein the polymer layer includes an enzyme, a recognition moiety, and a protecting moiety, where each of the enzyme, the recognition moiety, and the protecting moiety are on the outside surface of the polymer layer, wherein the hollow core has a diameter of about 1 to 5000 nm, wherein a therapeutic agent is disposed in the hollow core, wherein the therapeutic agent is present in a pharmaceutically effective amount to treat the condition, wherein the hollow nanozyme has pores in the polymer layer, wherein the therapeutic agent does not escape through the pores because of the protecting moiety on the polymer layer that substantially blocks the pores; wherein the hollow nanozyme enters a cell of the subject, wherein upon entering the cell the protecting moiety is released from the polymer layer and the therapeutic agent is released into the cell. In an embodiment, the condition to be treated can include viral diseases and cancer therapy, in particular, HBV, HCV, and HPV diseases, HCC, EBOV, and liver cancer.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A illustrates a scheme for the two-step growth of gold shell onto $Fe_3O_4$ nanoparticles: (1) the growth of thin gold shell in chloroform, and (2) the growth of thicker gold shell in an aqueous solution. FIG. 1B illustrates a typical TEM image of 10-nm $Fe_3O_4$ nanoparticles. FIG. 1C illustrates a typical TEM image of the resulting $Fe_3O_4$/Au core/shell nanoparticles with a shell thickness of 2.5 nm.

FIG. 2 illustrates a scheme for making $Fe_3O_4$/Au containing nanozymes: (1) loading of ribonucleases, (2) surface functionalization with a mixture of ss-DNA oligonucleotides and the oligonucleotides cross-linked with DNA aptamers of AS1411 and TSL11a using PEG spacers, and (3) surface functionalization with PEG-block-poly(L-lysine hydrobromide) copolymers.

FIGS. 6A and 6B illustrate transmission election microscope images of "matured" hollow nanozymes negatively stained with uranyl acetate.

FIG. 7 illustrates a scheme for making nanozymes loaded with sorafenib: (1) loading sorafenib into the nanozymes, and (2) surface functionalization with PEG-block-poly(L-lysine hydrobromide) copolymers, yielding "matured" nanozymes.

FIG. 8A shows one embodiment of a c-MET probe designed to specifically target and be reverse complementary to the CDS region of c-MET mRNA. FIG. 8B shows embodiments of a designed c-MET probe sequence (SEQ ID NO: 5) aligned with the target site (SEQ ID NO: 6) in the genome of c-MET (GenBank: XM_009454025.1).

FIG. 8C shows a schematic representation demonstrating the function and design of the c-Met nanozyme.

FIG. 9A shows schematic representation of different nanozyme used in experiment to evaluate the effect of the anti c-MET nanozyme on c-MET mRNA expression. Au-Rnase A: nanozyme loading only with enzyme; Au-probe DNA: nanozyme loaded only with c-MET probe DNA (SEQ ID NO: 5); c-MET NZ: nanozyme loaded with both c-MET probe DNA (SEQ ID NO: 5) and enzyme; HCV (Control) NZ: nanozyme loaded with HCV probe DNA (SEQ ID NO: 7) not matching with c-MET target mRNA and enzyme. FIG. 9B shows a graph demonstrating the results of qRT-PCR analysis of c-MET expression level treated with the different nanozymes of FIG. 9A. c-MET expression level was represented as the percentage of PBS control. Each bar presents the mean and standard deviation derived from three independent experiments; Student's t test: ns, nonsignificance P>0.05, **** for P 0.000022.

FIGS. 14A-14C show a schematic representation describing the design and function of an anti-EBOV nanozyme. FIG. 14A shows the specific targets for Probe 1 and probe 2, which are reverse complements to the EBOV cGP (+) and cGP (−) regions. FIG. 14B shows embodiments of the designed EBOV probes aligned with target site in the genome of Zaire EBOV (GenBank: KP728283). FIG. 14C shows a schematic depicting the function of the nanozyme.

FIGS. 15A-15D shows micrographic images demonstrating the anti-EBOV effects of the anti-EBOV nanozyme. Hybrid RNA JFH1/EBOV(+) and JFH1/EBOV(−) was transcribed from Xbal-linearized pJFH1/EBOV(+) and pJFH1/EBOV(−) plasmids. Huh7.5 cells were electroporation with transcribed RNA JFH1/EBOV(+) (FIGS. 15A-15B) and JFH1/EBOV(−) (FIGS. 15C and 15D) and cultured with 0.5 mg/ml G418 for 2 weeks. The selected clones were pooled and seeded on cover glasses in 24 well plates. The anti-EBOV nanozymes and control nanoparticles were added in 5 nM with every 2 days. Six days later, the cover glasses were subjected to immunostaining assay with mAb (HL1126) against HCV NS5A to evaluate the hybrid RNA replication ability.

DETAILED DESCRIPTION

Figure 3:
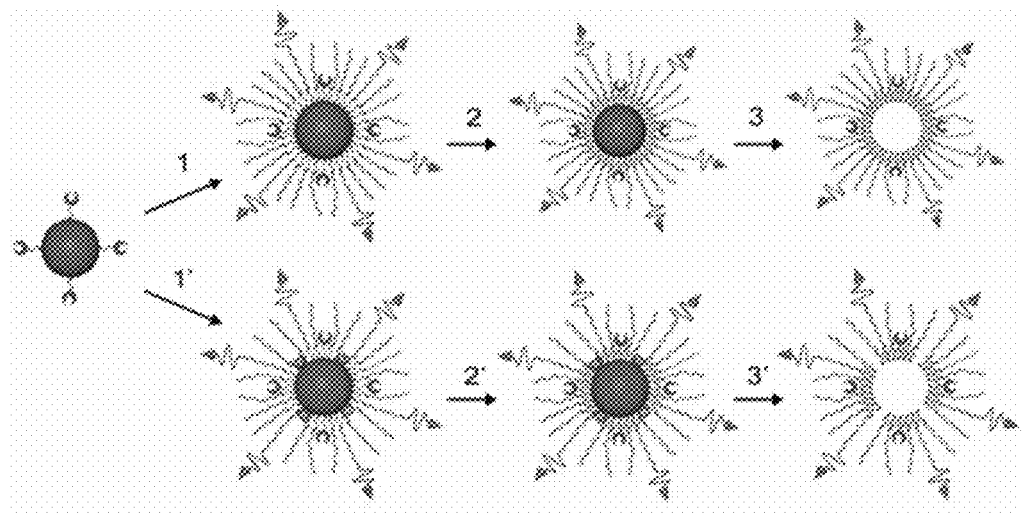
FIG. 3 illustrates a scheme for synthesizing hollow nanozymes from ribonuclease-functionalized gold nanoparticles: Step 1: Surface functionalization with a mixture of alkylthiol-terminated, propargyl-modified ss-DNA oligonucleotides and the oligonucleotides cross-linked with DNA aptamers of AS1411 and TSL11a using PEG spacers. For step 1', serum albumin is co-functionalized with ss-DNA oligonucleotides. Steps 2 and 2': cross-linking of the propargyl groups on the surface of the gold nanoparticle. Steps 3 and 3': removal of the gold nanoparticle scaffold using KCN solution.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of imaging, chemistry, synthetic organic chemistry, biochemistry, biology, molecular biology, microbiology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

By "administration" is meant introducing a nanozyme of the present disclosure into a subject. Any route of administration, such as intravenous, oral, topical, subcutaneous, peritoneal, intraarterial, inhalation, vaginal, rectal, nasal, introduction into the cerebrospinal fluid, or instillation into body compartments can be used.

As used herein, the term "subject" or "patient" includes humans, mammals (e.g., cats, dogs, horses, etc.), poultry, and the like. Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. The term "living subject" refers to a subject noted above that are alive. The term "living subject" refers to the entire subject and not just a part excised (e.g., a liver or other organ) from the living subject.

The term "sample" can refer to a tissue sample, cell sample, a fluid sample, and the like. The sample may be taken from a subject. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over the background signal.

The term "detectable signal" is a signal derived from analytical techniques such as, but not limited to, magnetic resonance imaging (MRI) or other appropriate device based on the construction of the nanozyme. The detectable signal is detectable and distinguishable from other background signals that may be generated from the subject. In other words, there is a measurable and statistically significant difference (e.g., a statistically significant difference is enough of a difference to distinguish among the detectable signal and the background, such as about 1%, 3%, 5%, 10%, 15%, 20%, 25%, 30%, or 40% or more difference between the detectable signal and the background depending on the circumstances) between detectable signal and the background. Standards and/or calibration curves can be used to determine the relative intensity of the acoustic detectable signal and/or the background.

The term "unit dosage form," as used herein, refers to physically discrete units suitable as unitary dosages for human and/or animal subjects, each unit containing a predetermined quantity of a compound (e.g., therapeutic agent used in the nanozyme, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the subject.

The terms "therapeutically effective amount" and "an effective amount" are used interchangeably herein and refer to that amount of a therapeutic agent or nanozyme including the therapeutic agent being administered that is sufficient to effect the intended application including, but not limited to, condition or disease treatment. For example, an effective amount of a therapeutic agent will relieve to some extent one or more of the symptoms of the disease, i.e., to some extent, one or more of the symptoms of the condition or disease. The therapeutically effective amount may vary depending upon the intended application (in vitro or in vivo), or the subject and condition being treated, e.g., the weight and age of the subject, the severity of the condition, the manner of administration and the like, which can readily be determined by one of ordinary skill in the art. The term also applies to a dose that will induce a particular response in target cells or tissue. The specific dose will vary depending on the particular therapeutic agent chosen, the dosing regimen to be followed, whether it is administered in combination with other agents, timing of administration, the cells or tissue to which it is administered, and the physical delivery system in which it is carried.

General Discussion

Embodiments of the present disclosure provide for nanozymes having a nanoparticle (including, but not limited to, a core/shell nanoparticle), hollow nanozymes, hollow nanozymes including a therapeutic agent, methods of making nanozymes, methods of using nanozymes, and the like. One or more of the embodiments of the present disclosure may be advantageous because they can be designed to be selective, may not produce an elicit immune response, can have an extended life time, can be stabile for longer periods of time, and/or can deliver therapeutic agents, relative to other enzyme based products. Embodiments of the present disclosure can be used to image, detect, study, monitor (e.g., survival), evaluate, and/or treat, a condition such as a disease using an embodiment of the nanozyme or hollow nanozyme. Embodiments of the present disclosure can be administered to a subject. In some embodiments, the subject can have or be suspected of having hepatitis B virus (HBV) disease, hepatitis C virus (HCV) disease, human papilloma virus (HPV) disease, hepatocellular carcinoma (HCC), ebola virus (EBOV) disease, or a liver cancer. Embodiments of the present disclosure can be used to treat viral diseases and used in cancer therapy, in particular, HBV, HCV, and HPV diseases, HCC, ebola EBOV, and liver cancer. Additional details are described in the Examples.

In general, three embodiments of nanozymes are described herein, where each can include a number of variations. In some embodiments, the nanozymes contain a nanoparticle core. The nanoparticle core can include metal, such as a noble metal and composites thereof. In some embodiments the nanoparticle core has a homogenous structure with composition of a metal, a metal oxide, or a semiconductor. In other exemplary embodiments, the nanoparticle core of the nanozyme has a heterogeneous core/shell configuration, such as a $Fe_3O_4$/Au core/shell nanoparticle. In an embodiment, the superparamagnetic properties of $Fe_3O_4$/Au nanoparticles enable tracking the corresponding nanozymes in vivo using magnetic resonance imaging (MRI). In addition, embodiments of the present disclosure can be used in photothermal therapy (e.g., via the gold shell) and magnetic resonance imaging (e.g., iron core), in conjunction with the other capabilities of the nanozyme.

Another exemplary embodiment includes a hollow nanozymes that does not include an inorganic nanoparticle (e.g., a hollow area or core where the nanoparticle would be otherwise located). In an embodiment, the hollow nanozyme can include a label (e.g., a dye label) for imaging. Hollow nanozymes without inorganic nanoparticles exhibit a hollow core (where a nanoparticle was previously present), where the removal of the nanoparticle eliminates the potential long-term toxicity that might be induced by the inorganic nanoparticles. In addition, the hollow nanozymes labeled with a dye, such as fluorescein, can be tracked using fluorescence microscopy.

Another exemplary embodiment includes hollow nanozymes including a therapeutic agent (e.g., a small-molecule drug) disposed within the hollow area of the hollow nanozyme. Small-molecule drug loaded hollow nanozymes are expected to have enhanced anticancer efficacy.

In an embodiment, the nanoparticle containing nanozyme ("nanoparticle nanozyme") or the hollow nanozyme can include two or more types of ss-DNA oligonucleotides, and this design allows nanozymes to have multi-targeting capability in degradation of the mRNA of survivin (or bcl 2 mRNA or other mRNAs) at different positions or the mRNAs of both of these or other proteins.

Because of the architecture of the nanozymes described herein (i.e. nanoparticle nanozymes and hollow nanozymes), their enzymatic activity and target sequence specificity can be maximized through the optimization of one or more of the following parameters: the size of nanoparticle scaffolds, the density and composition of RNA endonucleases, the density, and/or sequence and length of ssDNA oligonucleotides. The cell-type targeting specificity of the various embodiments of nanozymes described herein can be determined by the density of DNA-aptamer based guiding components and the density of the PEG-based protection components. The endosomal escape capability of the nanozymes is dependent on the density and composition of endosomal escape enhancing components. In addition, these parameters also play a part in the efficiency of nanozyme cell entry, stability, and/or toxicity.

Now referring to the nanoparticle nanozymes. The nanoparticle nanozymes can include a nanoparticle, an enzyme, and a recognition moiety. In embodiments, the nanoparticle can have a core/shell configuration as previously described. In other embodiments, the nanoparticle does not have a core/shell configuration as previously described. Each of the enzyme and the recognition moiety are attached (e.g., directly or indirectly via a linker (e.g., compound or protein) or the like) to a surface of the nanoparticle of the nanozyme. In some embodiments, the recognition moiety and/or the recognition moiety is attached to a polymer layer on the surface of the nanoparticle. In an embodiment, the nanoparticle nanozyme can include two or more types (e.g., have different functions) of enzymes and/or recognition moieties. In further embodiments, the nanozyme can also include a protection moiety, an inter- and intra-cellular traffic guiding moiety, and/or an allosterically functional moiety.

In an embodiment, the nanoparticle can function as a scaffold for the other components to attach. In an embodiment, the nanoparticle can also function as a detectable nanoparticle (e.g., that has or is able to produce a detectable signal) that can be detected using imaging methods such as MRI or a photothermal therapy agent for disease (e.g., cancer) treatment.

In some embodiments, the nanoparticle includes a noble metal. In some embodiments, the nanoparticle includes a core and a shell disposed on the core (a "core/shell" configuration). In an embodiment, the nanoparticle can include a $Fe_3O_4$/Au core/shell nanoparticle, a $Fe_2MnO_4$/Au core/shell nanoparticle, a $Fe_2ZnO_4$/Au core/shell nanoparticle, or a FePt/Au core/shell nanoparticle. In some embodiments, the nanoparticle does not have a core/shell configuration. In some of these embodiments, the nanoparticle can be a noble metal or noble metal composite nanoparticle, such as Au.

In an embodiment, the nanoparticles can be isotropic shaped such as spherical, cubic, tetrahedron, polyhedron, or anisotropic shaped such as a nanoplate, a nanorod, a nanowire, and a nanoprism. In an embodiment, the dimension of the core/shell nanoparticle can be about 1 to 5100 nm, about 1 to 1000 nm, or about 1 to 500 nm, in diameter for spherical or near spherical nanoparticles (or the longest distance along a cross-section of the nanoparticle). In an embodiment, the core can have a diameter of about 1.0 to 20 nm or about 20 to 5000 nm. In an embodiment, the shell can have a thickness of about 1.0 to 5.0 or about 5.0 to 100 nm.

In an embodiment, the enzyme can function to act upon a nucleotide (e.g., DNA, RNA, or smaller nucleotide) or a peptide (e.g., protein). In an embodiment, the enzyme functions include hydrolysis, methylation, de-methylation, phosphorylation, de-phosphorylation, ubiquitylation, oxidation, reduction, nucleic acid editing, condensation, or other like enzymatic modifications for DNA, RNA, proteins, peptides, oligosuccharides, polysaccharides, or small molecules such as neuron transmitters. In an embodiment, the enzyme does not react with the recognition moiety and the optional protecting moiety when attached to the nanoparticle (or the polymer layer of the hollow nanozyme) or does not substantially react (e.g., can react at a rate with the recognition moiety and/or the protecting moiety so that the nanozyme can be used to accomplish the desired goals and/or perform the desired function(s) of the nanozyme) with the recognition moiety and the protecting moiety when attached to the nanoparticle (or the polymer layer of the hollow nanozyme).

In an embodiment, the enzyme can include endoribonucleases, endodeoxyribonuclease, endoproteinase, or a combination thereof. In an embodiment, the endoribonuclease can include: RNase A, RNase III, RNase H, RNase P, or RNase T1. In an embodiment, the endodeoxyribonuclease can include: deoxyribonuclease II, deoxyribonuclease IV, restriction enzyme, and UvrABC endonuclease. In an embodiment, the endoproteinase can include: proteinase K, trypsin, chymotrypsin, elastase, thermolysin, pepsin, and endopeptidase V8. In an embodiment, the nanozyme can include 1 to 200 enzymes attached to the nanoparticle or the polymer layer of the hollow nanozyme.

In an embodiment, the recognition moiety can function to cause the nanozyme (any of those described herein) to interact with a molecule(s). In an embodiment, the recognition moiety can have an affinity for a cell, a tissue, a protein, DNA, RNA, an antibody, an antigen, and the like, that may be associated with a condition, disease, or related biological event, of interest. In particular, the recognition moiety can function to target specific DNA, RNA, and/or proteins of interest. The recognition moiety can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, aptamers, small molecules, ligands, or combinations thereof, that have an affinity for a condition, disease, or related biological event or other chemical, biochemical, and/or biological events of the condition, disease, or biological event. In an embodiment, the recognition moiety can include: sequence-specific DNA oligonucleotides, locked nucleic acids (LNA), and peptide nucleic acids (PNA), antibodies, and small molecule protein receptors. In an embodiment, the nanozyme (any of the embodiments described herein) can include 1 to 2000 recognition moieties attached to the nanoparticle or the polymer layer of the hollow nanozyme. In an embodiment, the recognition moiety can also include the function(s) of the protecting moiety, and/or inter- and intra-cellular traffic guiding moiety so that the recognition moiety has multiple (e.g., ternary) functions. The function(s) of the protecting moiety are described herein.

In an embodiment, the nanozyme (any embodiment described herein) can also include a protecting moiety. The protecting moiety can be attached (e.g., directly, indirectly via a linker (e.g., compound or protein), or the polymer layer of the nanozyme, or the like) to the nanoparticle or the polymer layer of the hollow nanozyme. In an embodiment, the protecting moiety can function to control the intracellular stability, dispersibility, cell-uptake efficiency, and/or selective cell-entry efficiency. Alternatively or in addition, the protecting moiety can substantially reduce (e.g., reduce by about 70% or more, about 80% or more, about 90% or more, about 95% or more, or about 99% or more relative to not including the protecting group) or eliminate the toxicity of the nanozyme and/or substantially reduce (e.g., reduce by about 70% or more, about 80% or more, about 90%, or more, about 95% or more, or about 99% or more, relative to not including the protecting group) or eliminate the immunogenicity of the nanozyme, or a combination thereof. In an embodiment, the protecting moiety can reduce (e.g., reduce by about 70% or more, about 80% or more, about 90% or more, about 95% or more, or about 99% or more relative to not including the protecting group), or eliminate non-target molecules from approaching the enzymes of the nanoenzyme, and can protect the enzyme moiety of the nanozyme from degradation by enzymes (e.g., proteinases).

In an embodiment, the protecting moiety can include: DNA oligonucleotides, locked nucleic acids (LNA), peptide nucleic acid (PNA), poly(ethylene glycol) (PEG), poly(vinyl alcohol) (PVA), poly(acrylic acid) (PAA), poly(propylene furmarate-co-ethylenee glycol) (P(PF-co-EG)), polyacrylamide, polypeptides, poly-N-substituted glycine oligomers (polypeptoids), hyaluronic acid (HA), alginate, chitosan, agarose, collagen, fibrin, gelatin, dextran, and any combination thereof, as well as derivatives of each of these ligands and the like. In an embodiment, the nanozyme (any of those described herein) can include 1 to 2000 protecting moieties attached to the nanoparticle or the polymer layer of the hollow nanozyme. In an embodiment, the nanozyme can include two or more types (e.g., have different functions) of enzymes, protecting moieties, and/or recognitions moieties.

In an embodiment, the inter- and intra-cellular traffic guiding moiety can guide a nanozyme (any of these described herein) into specific organs (such as liver), cell types (such as Hepatocyte), sub-cellular organelles, and nucleus. The inter- and intra-cellular traffic guiding moiety can be attached (e.g., directly, indirectly via a linker (e.g., compound or protein), or the polymer layer of the nanozyme, or the like) to the nanoparticle or the polymer layer of the hollow nanozyme. In an embodiment, the inter- and intra-cellular traffic guiding moiety can include DNA oligonucleotides, locked nucleic acids (LNA), peptide nucleic acid (PNA), cyclodextrin, polymers, TransFectin, and any combination thereof, as well as derivatives of each of these ligands and the like. In an embodiment, the nanozyme can include 1 to 2000 inter- and intra-cellular traffic guiding moiety attached to the nanoparticle or the polymer layer of the hollow nanozyme. In an embodiment, the nanozyme can include two or more types (e.g., have different functions) of enzymes, protecting moieties, and/or recognitions moieties, and/or inter- and intra-cellular traffic guiding moieties.

In addition, the allosterically functional moiety can also be attached onto the nanozyme. The allosterically functional moiety can be attached (e.g., directly, indirectly via a linker (e.g., compound or protein), or the polymer layer of the nanozyme, or the like) to the nanoparticle or the polymer layer of the hollow nanozyme. The allosterically functional moiety enables the nanozyme to have an on/off switch in response to chosen allosteric effectors such as specific products or byproducts (e.g., glucose) in disease-associated metabolism pathways. In an embodiment, the allosterically functional moiety can include DNA, RNA, peptide nucleic acid (PNA), locked nucleic acid (LNA), a peptide, a protein, a sugar, a lipid, a small molecular receptor such as biotin, cyclodextrin, a polymer, TransFectin, and a combination thereof, as well as derivatives of each of these moieties and the like.

In addition to the enzyme, the recognition moiety, the protecting moiety, and/or inter- and intra-cellular traffic guiding moieties, the nanozyme can include a therapeutic agent such as a drug that can be used to treat the disease or condition of interest that is attached to the surface of the nanozyme.

In an embodiment, the hollow nanozyme can include a polymer layer surrounding a hollow core. An embodiment of the polymer layer can include and/or have attached thereto (e.g., directly or indirectly), an enzyme, and a recognition moiety. In an embodiment, each of the enzyme and the recognition moiety are attached (e.g., directly, indirectly via a linker (e.g., compound or protein) or the like) to the polymer layer. In an embodiment, the hollow nanozyme can include two or more types (e.g., have different functions) of enzymes and/or recognition moieties. In an embodiment, the hollow nanozyme can also include a protection moiety, an inter- and intra-cellular traffic guiding moiety, and/or an allosterically functional moiety, where each individually can be attached thereto (e.g., directly or indirectly). Each of the moieties described in regard to the hollow nanozyme are the same or similar to those described above in reference to the core/shell nanoparticle nanozyme.

In an embodiment, the hollow core bound by the polymer layer can have a dimension of about 1 to 5000 nm, about 1 to 1000 nm, or about 1 to 500 nm, in diameter for spherical or near spherical nanoparticles (or the longest distance along a cross-section of the nanoparticle). In an embodiment, the polymer layer can have a thickness of about 1 to 50.

In an embodiment, the polymer layer can be formed by the crosslinking of one or more of the following: the enzyme, the recognition moiety, and the protecting moiety, or other moiety of the nanozyme. In an embodiment, the crosslinking can occur at or near one end of: the enzyme, the recognition moiety, the protecting moiety, or other moiety, so that the hollow core area is surrounded by the polymer layer. In an embodiment, the polymer layer can be made of a polyalkyne, polyolefin, polyisoprene, polyamide, polyester, polycarbonate, silicones, co-polymers of these, combinations of these, and the like. In an embodiment, the precursor (e.g., alkyne) to the polyolefin can be a part of or a function group of one more of: the enzyme, the recognition moiety, the protecting moiety, or other moiety, where the precursor is disposed at or near the end closest to the hollow area (or prior to the hollow area, the nanoparticle). In an embodiment, one or more of the enzyme, the recognition moiety, the protecting moiety, or other moiety, can be separately attached to the polymer layer after or during formation of the polymer layer.

In an embodiment, the polymer layer includes a plurality of pores through the polymer layer. The pores can have a diameter of about 0.2 to 10 nm or 5 to 200 nm. The pore diameters can be the same or different.

In an embodiment, an imaging agent can be attached to the hollow nanozyme. In an embodiment, the imaging agent can include a dye, metal oxide nanoparticle, metal nanoparticle, semiconductor nanoparticle quantum dots, and diamond nanoparticle. In an embodiment, the imaging agent can be attached (e.g., directly or indirectly) to the hollow nanozyme or be within the hollow core. An appropriate detection system can be used to detect or image the nanozyme.

As mentioned above, a therapeutic agent can be disposed in the hollow core. As described in more detail herein, the therapeutic agent can be disposed in the hollow core through the pores. Then a moiety, such as the protection moiety, can be used to substantially prevent or prevent the therapeutic agents from being released from the hollow core until interaction with the targeted cells related to the condition or disease.

In an embodiment, the amount of therapeutic agent included in the hollow core can be about 1 to $10^{15}$ molecules. However, the amount can be adjusted based on the size of the hollow core, condition or disease to be treated, others moieties present on the hollow nanozyme (in some instances, the therapeutic agent and the moiety can act synergistically), and the like.

In an embodiment, the therapeutic agent can be a small molecule drug, peptide-based drugs, protein-based drugs such as interferon nucleic acid-based drugs such as short-interfering RNA, and polymer drug conjugates, and the like.

In an embodiment, the hollow nanozyme can be made from a nanozyme having a nanoparticle. In an embodiment, the nanozyme includes a nanoparticle core that can be removed to produce a hollow core. In an embodiment, the nanoparticle can include a metal (e.g., gold and silver), a metal oxide (e.g., iron oxide and zinc oxide), or a semiconductor (e.g., CdSe and InP).

In an embodiment, the method includes a nanozyme having a nanoparticle core, where an enzyme, a recognition moiety, and a protecting moiety, as well as other possible moieties discussed herein (e.g., a protection moiety, an inter- and intra-cellular traffic guiding moiety, and/or an allosterically functional moiety), are attached (e.g., each independently, directly or indirectly) to the surface of the nanoparticle core. A polymer layer can be formed from a portion of one or more of the following: the enzyme, the recognition moiety, the protecting moiety, and the like. In an embodiment, the polymer layer can be formed at or near one end of: the enzyme, the recognition moiety, the protecting moiety, and the like, so that the polymer layer surrounds the nanoparticle core. Additional details about the polymer layer are described above. Once the polymer layer is formed, the nanoparticle core can be removed leaving the polymer layer surrounding a hollow core.

In an embodiment, the nanozyme can include a pore-forming moiety. In an embodiment, the pore-forming moieties are disposed on the surface of the nanoparticle prior to forming the polymer layer (described below). The polymer layer can be formed around the pore-forming moieties, so that upon removal of the pore-forming moieties, a pore is formed through the polymer layer. In an embodiment, the pore-forming moiety can be removed by removing the nanoparticle. In an embodiment, the pore-forming moiety can be removed separately from the removal of the nanoparticle. In an embodiment, the pore-forming moiety can include a protein, polymer, nanoparticle, micelle, liposome, and a combination thereof. In an embodiment, about 1 to 5000 pore-forming moieties can be disposed on the nanoparticle surface.

In an embodiment, the hollow nanozyme can be loaded by disposing a hollow nanozyme including pores in a solution including the therapeutic agent. In an embodiment, the therapeutic agents can be disposed (e.g., flow) into the hollow area through the pores. Once the therapeutic agents are within the hollow area of the hollow nanozyme, a protecting moiety can be disposed onto the polymer layer. The protecting moiety substantially blocks the pores so the therapeutic agent does not exit the pores. In an embodiment, the protecting moieties can be removed as the hollow nanozyme enters the cell of interest, and upon removal of the protecting moieties, the therapeutic agent is released into the cell. In an embodiment, the protecting moieties can be removed in the presence of certain agents that exist (e.g., produced by) around certain types of cells (e.g., cancer cells), virus (e.g., HCV), and the like.

As mentioned above, the hollow nanozyme can include an imaging agent so that the location of the hollow nanozymes can be determined.

Kits

This disclosure encompasses kits, which include, but are not limited to, nanozymes, and directions (written instructions for their use). The components of the nanozyme can be tailored to the particular disease, condition, or even being studied and/or treated. The kit can further include appropriate buffers and reagents known in the art for administering various combinations of the components listed above to the host cell or host organism.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1. Synthesis of $Fe_3O_4$/Au Core/Shell Nanoparticles

The $Fe_3O_4$/Au core/shell nanoparticles exhibit the superparamagnetic properties of the core, the surface plasmon resonance absorption of the Au shell, and the surface functionalization chemistry of the Au shell. These nanoparticles have low toxicity, and they are $T_2$ contrast agents for MRI and contrast agents for transmission electron microscope (TEM). The $Fe_3O_4$ nanoparticle cores can be synthesized through the thermal decomposition of iron oleate at elevated temperatures ranging from about 280 to 340° C., and our preliminary studies have shown that the sizes of the resulting iron oxide nanoparticles are readily determined by the reaction temperature.[1]

The gold shell was grown in a two-step process (FIG. 1). In the first step, a thin shell (~1 nm) was grown onto $Fe_3O_4$ nanoparticle cores at 50° C. in a chloroform solution containing oleylamine. $AuCl_3$ was used as the gold precursor and oleylamine as the reducing agent and capping ligand. The resulting nanoparticles was transferred into aqueous solution using cetyltrimethylammonium bromide (CTAB) and sodium citrate. In the second step, $HAuCl_4$ was used as the precursor and ascorbic acid was used as the reducing agent. These results demonstrate that the two-step approach allows the growth of uniform gold shells up to 20 nm in thickness. Interestingly, the water soluble core/shell nanoparticles can form ordered monolayers in the presence of 0.03 M NaCl (FIG. 1C). In this study, we choose $Fe_3O_4$ nanoparticle cores smaller than 14 nm for their superparamagnetic properties, and we have synthesized $Fe_3O_4$/Au core/shell nanoparticles with sizes ranging from 6 nm to 45 nm for the optimization of nanozymes. The products of each step is thoroughly identified using a variety of techniques including UV-Vis absorption, dynamic light scattering, TEM, X-ray diffraction (XRD), and superconducting quantum interference device (SQUID).

Example 2: Synthesis of Nanozyme Containing $Fe_3O_4$/Au Nanoparticles

The nanozyme can be synthesized via a three-step surface functionalization of $Fe_3O_4$/Au nanoparticles: (i) functionalization with RNA endonucleases, (ii) functionalization with a mixture of alkylthiol-terminated ssDNA oligonucleotides with one or more RNA recognition sequences and aptamer-contained strands, and (iii) functionalization with copolymers of PEG-block-poly(L-lysine hydrobromide) as components for both protection and endosomal escape enhancement (FIG. 2). We choose RNase A or a mixture of RNase A and RNase H for the nanoparticle modification, and these enzymes bind onto the gold surface of $Fe_3O_4$/Au nanoparticles through nonspecific interactions.[2]

In the second step, alkylthiol-terminated ssDNA oligonucleotides can be functionalized onto nanoparticles using gold-thiol binding chemistry. The sequences of ssDNA oligonucleatides are chosen according to the antisense sequences of the mRNAs of survivin and bcl 2. Specifically, we design the sequences of alkylthiol functionalized oligonucleotides for making nanozymes according to two antisense sequences of survivin mRNA (1) 5'TGTAGAGATGCGGTGGTCC3' (SEQ ID NO: 1) and (2) 5'GATGGCACGGCGCACTTTC3', (SEQ ID NO: 2) and two antisense sequences of bcl 2 mRNA: (1) 5' GGTCTGCAGCGGCGAGGTCCTG3' (SEQ ID NO: 3) and (2) 5'GTCTGCAGCGGCGAGGTCCTG3'(SEQ ID NO: 4). In addition, AS1411 and TSL11a aptamers can be crosslinked at the 5'end of these alkylthiol functionalized oligonucleotides with PEG spacers (FIG. 2). These crosslinked molecules were synthesized using DNA synthesizer with commercialized reagents from Glen Research, Inc. The number of crosslinked molecules loaded onto nanoparticles and the number of PEG spacers in these molecules are adjusted to improve the stability and the cell-type targeting specificity of nanozymes.

Moreover, oligonucleotide density on nanozymes are controlled in the synthesis, and are quantitatively measured using a literature method.[2] In general, the density of oligonucleotides should be high enough to block the access of the enzymes to non-complementary ssRNAs, however, if the density is too high, oligonucleotides could also block the access of the enzymes to the complementary ssRNA and decrease nanozyme activity of nanozymes. Furthermore, a major technical difficulty is the removal of unbound RNAs from nanozyme samples. These unbound enzymes significantly interfere with the in vitro tests of the enzymatic activity and target specificity of nanozyme. In preliminary studies, we have established a procedure to overcome this difficulty. This procedure includes separations using affinity chromatography and multiple centrifugations.

In the third step, methoxy-PEG-block-poly(L-lysine hydrobromide) copolymers are functionalized onto the surface of nanoparticles, yielding "matured" nanozymes. These copolymers bind onto the surface of nanoparticles via electric static interactions between the positively charged poly-lysine domain and negatively charged oligonucleotides. A number of these copolymers are commercially available from companies such as Alamanda Polymers, Inc. We have adjusted the number of L-lysine units repeating in the copolymer to optimize endosomal escape capability and the structural stability of nanozymes, and have adjusted the number of the ethylene glycol repeating units to minimized the non-specific binding level of the nanozyme and maximize their stability in biological environments.

Example 3: Synthesis of Hollow Nanozyme without Inorganic Nanoparticle Cores

Figure 4:
FIG. 4 illustrates a schematic for cross-linking RNase and succinimidyl-4-formylbenzamide DNA oligonucleotide through succinimidyl-6-hydrazino-nicotinamide.

The removal of the inorganic nanoparticle cores can effectively eliminate the potential long-term toxicity of nanozymes induced by the core, and create a cavity for loading and delivery of small molecule drugs (such as sorafenib) for cancer treatment. To make core-removable nanozymes, we have modified RNA endonucleases and recognition ss-DNA oligonucleotides with alkylthiol-terminated sequences of poly-thymine (T) bases modified with propargyl ether groups linked through an amidohexylacrylamido linker to the 5 position of the T base, and a subsequent spacer of six unmodified T bases for flexibility and accessibility of the remaining moieties. RNA endonucleases with single alkylthiol-terminated, propargyl ether modified poly-thymine (T) sequences were synthesized using a standard protein-oligonucleotide conjugation kit from Solulink, Inc, and purified using gel electrophoresis (FIG. 4).

Two types of hollow nanozyme have been synthesized: hollow nanozyme with continuous shell (FIG. 3 (top)) and hollow nanozyme with porous shell (FIG. 3 (bottom)). The synthesis begins with the surface modification of gold nanoparticles with alkylthiol-terminated and propargyl-ether-modified RNA endonucleases via gold/thiol linking chemistry. After purification, the resulting nanoparticles are further treated in the following three steps to yield hollow nanostructures (FIG. 3).

In the first step, the RNase-modified gold nanoparticles are functionalized with propargyl-ether containing, alkylthiol-terminated oligonucleotides via gold/thiol linking chemistry, or co-functionalized with a specific protein (e.g., human serum albumin) for hollow nanozyme with porous shell that can load and deliver small molecule drugs. The protein serves as "pore-making agent;" it binds onto the surface of gold nanoparticle via nonspecific interactions, creating areas without alkylthiol-terminated, propargyl-ether modified poly-thymine (T) sequence on the gold nanoparticle surface, leading to the formation of hollow nanozymes with porous shell (FIG. 3). The pore size are controlled by the size of the pore-making protein molecules.

In the second step, during room temperature incubation at phosphate-buffered saline (0.15 M), cross-linking takes place between the propargyl groups on the surface of the gold nanoparticle and along the modified T bases, yielding a densely packed, cross-linked DNA shell on the surface of gold nanoparticles. In the third step, gold nanoparticle scaffolds are removed with an aqueous KCN solution (1 μM)[3] and the resulting hollow nanostructures are purified through multiple centrifugations. The hollow nanostructures made with serum albumin functionalization at the initial step are expected to have holes on the DNA shells because of the removal of serum albumin with gold nanoparticle scaffolds (FIG. 3). The structural stability of the resulting nanostructures have been optimized by fine-tuning the density of propargyl-ether modified poly-thymine (T) sequences on the surface of the nanoparticles. In principle, these hollow nanostructures without an inorganic nanoparticle scaffold should exhibit more structural flexibility and thus we would expect that these nanostructures can have high enzymatic activity again RNA targets as compared with those ones containing an inorganic nanoparticle scaffold. The enzymatic activity and target specificity are evaluated through in vitro and in vivo tests.

Figure 5:
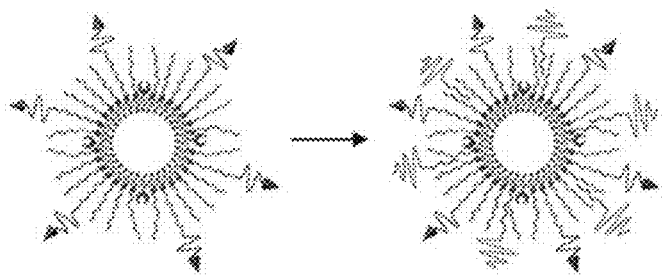
FIG. 5 illustrates a surface functionalization of DNA-RNase hollow nanostructures with PEG-block-poly(L-lysine hydrobromide) copolymers, yielding "matured" nanozymes.

Hollow nanostructures without holes are further functionalized with methoxy-PEG-block-poly(L-lysine hydrobromide) polymers, creating "matured" nanozymes (FIG. 5, FIG. 6). The oligonucleotide for making these nanozymes can be modified with fluorescein during the solid-state DNA synthesis using fluorescein phosphoramidite. Therefore, these resulting nanozymes can be used for the evaluation of their endosomal-escape capabilities using fluorescence microscopy with endosome labeling dyes.

In addition, we have determined the capacity of hollow nanostructures with surface holes for loading small molecule drug (such as anti-cancer, anti-virus, and anti-bacterial drugs, FIG. 7). We choose sorafenib as a model because of its known anticancer effects on liver cancer cells. In principle, sorafenib binds to densely packed and crosslinked thymine region of nanozyme with hydrogen bonding and π-π interactions, and thus sorafenib can be loaded into the cavity of nanozymes. Because hydrogen bonding and π-π interactions are very weak intermolecular interactions, the loaded sorafenib can be released from nanozymes. Because of the RNA degradation function of nanozymes, we expect that a very low dose of sorafenib would be required to create a potent anticancer effect against liver cancer cells in vitro and in vivo. Sorafenib release is due to the loose of the methoxy-PEG-block-poly(L-lysine hydrobromide) polymers from the nanozymes during endosomal escape. Moreover, the sorafenib loading capacity and release rate is dependent on pH, wherein sorafenib is loaded at a high pH (e.g., 8.5) and released at a low pH (e.g., 6.0), which is the endosomal pH). The sorafenib loading capacity and release rate as a function of pH is evaluated using assays based on optical spectroscopy.

Example 4: Testing the Activity and Specificity of Nanozymes

We have used $Fe_3O_4$/Au containing nanozyme to evaluate and optimize enzymatic activity and target specificity. First, the activity and specificity of nanozymes are measured using specific RNA molecular beacons, which contain a fluorophore on one end and a quencher on the other. Once cleaved by nanozymes, the fluorophore is separated from the quencher, and emits strong fluorescent light that is detected by a fluorometer. The results from these molecular beacon experiments are used as the initial guideline for refining the design and synthesis of nanozymes. Second, the activity and specificity of nanozymes are further determined using in vitro transcribed HCV or survivin RNA as the substrate and the in vitro transcribed host-keeping gene GADPH as a control. Electrophoresis and Northern blotting was used to quantify nanozyme activity and specificity. These results are used as initial feedback for the refinement of the structure design and the synthesis of nanozymes.

REFERENCES FOR EXAMPLES 1-4

1. Lynch, J.; Zhuang, J.; Wang, T.; LaMontagne, D.; Wu, H.; Cao, Y. C. "Gas-Bubble Effects on the Formation of Colloidal Iron Oxide Nanocrystals," *J. Am. Chem. Soc.* 2011, 133, 12664-12674.
2. Wang, Z.; Liu, H; Yang, S. H; Wang, T.; Liu, C.; Cao, Y. C. "Nanoparticle-based Artificial RNA Silencing Machinery for Antiviral Therapy." *Proceedings of the National Academy of Sciences*, 2012, 109, 12387-12392.
3. Cutler, J. I.; Zhang, K.; Zheng, D.; Auyeung, E.; Prigodich, A. E.; Mirkin, C. A. "Polyvalent Nucleic Acid Nanostructures," *J. Am. Chem. Soc.* 2011, 133, 9254-9257.

Example 5: c-Met Nanozymes

Background

Hepatocellular carcinoma (HCC) is the most aggressive and lethal form of primary liver cancer.[1,2] Systemic chemotherapy is offered to more than 80% of patients diagnosed at advanced stage with widespread unresectable tumors. The efficacy of current therapies is dismal, partially due to the great heterogeneity in tumor microenvironment and strong chemo-resistance. Serving as a hub for multiple heterogeneous signaling networks, Hepatocyte Growth Factor (HGF) and its receptor tyrosine kinase (MET) highly present in HCC and possibly link to cancer stem cells (CSC), a discrete sub-population exhibits numbers of traits required for tumorigenesis, provides an interesting avenue to study cancer.[3-5] Extensive evidence for the involvement of HGF/MET in multiple aspects of tumorigenicity in various types of cancer, including HCC, suggests targeting this signaling pathway could be of significant benefit in cancer drug development. Recent therapeutic strategies to target HGF/MET signaling has focused on development of (1) competitive inhibitors of HGF/MET (Ficlatuzumab, NK4), (2) monoclonal antibodies directed against HGF and MET (AMG102, MetMAb), and (3) small-molecule tyrosine kinase inhibitors directed against MET (Tivantinib, Foretinib, SAR844, BMS777607).[6]

Several MET inhibitors and antagonists have been used in preclinical and clinical studies but none of them provide promising outcome. Factors relating to limitations in drug delivery, toxic side effects, and/or inadequate accumulation in tumors resulting in reduced efficacy, etc., each partially accounts for the failure of these treatments. This Example demonstrates a nanozyme that can mimic the RNA-induced silencing complex for specific mRNA cleavage. The nanozymes provided herein can be advantageous over current treatments because they can (1) specifically target MET-driven signaling pathway by cleaving MET mRNA in an independent manner to cellular mechanism, (2) minimize off-target side effect and reduce toxicity to healthy cells, and (3) overcome and/or reduce drug resistance. The c-Met nanozymes can offer, inter alia, a great benefit to support the evaluation of HGF/MET as a potential therapeutic target for cancer treatment.

Figure 8A:
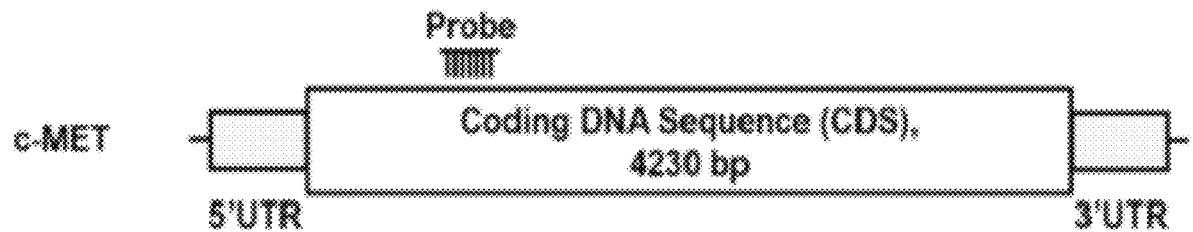
FIGS. 8A-8C show a schematic representation of describing the design and function of a c-MET nanozyme.
Figure 8B:
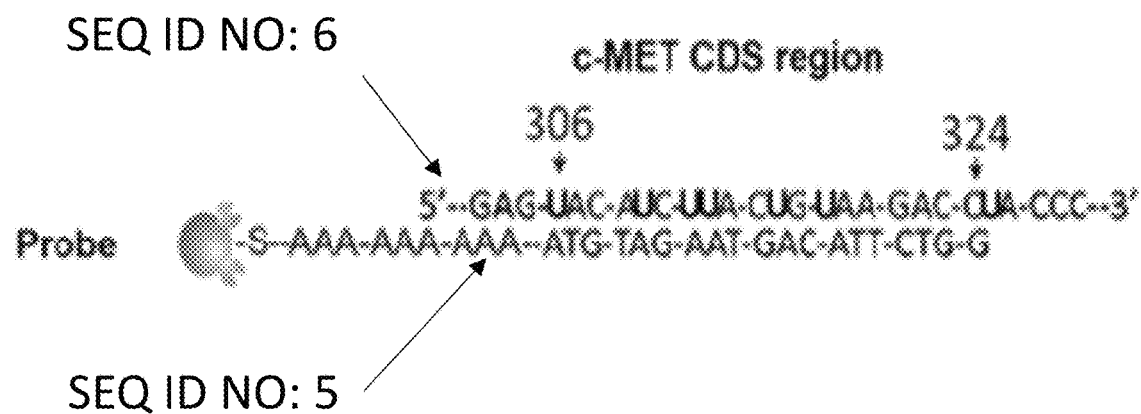
Figure 8C:
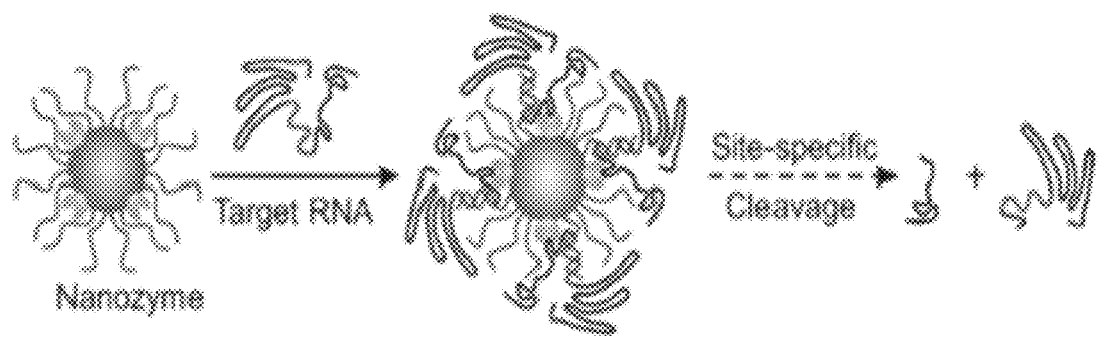

Design of c-MET Nanozyme Probe:

13 nm Au nanoparticles were used as the backbone for nanozyme synthesis due at least in part to their low toxicity and unique surface chemical properties for alkylthiol functionalization. A DNA probe (5'-GGT-CTT ACA GTA AGA TGT AAA AAA AAA A-SH-3') (SEQ ID NO: 5) (also referred to in this specification as a recognition moiety) was intentionally designed to bind with the conserved region of c-MET gene (306-324) and 9-A bases were inserted between the nanoparticle surface and the 19-nt recognition sequence for increasing the efficiency of the hybridization between a nanozyme and its complementary target (FIGS. 8A-8C). RNase A was used as the endoribonuclease component because it does not degrade the DNA-based recognition moiety of nanozymes, and it is one of the most robust and active ribonucleases for sequence nonspecific degradation of single-stranded RNAs, which have routinely been used for the removal of RNA contamination from DNA preparations as well as the removal of unhybridized regions of RNA from DNA/RNA or RNA/RNA hybrids.

Nanozyme Synthesis:

For the synthesis of NZs[7], 10 nM Au NPs can be mixed by shaking with 0.5 μM Rnase A (2 mL, 1.3 mM $Na_2CO_3$ pH 9.8) for 30 min under room temperature. Then 6.4 nmol probe DNA can be added in and the solution is can be turned into 10 mM phosphate pH 7.4. After 8 h of shaking under room temperature, NaCl (1.5 M) can be added gradually in to bring the NaCl concentration to 0.3 M in 32 h. The solution can then be further shaken for 8 h. The NZs can then be purified by centrifugation (13,000 rpm, 30 min 3 times) and redispersed in PBS (137 mM NaCl, 2.7 mM KCl, 10 mM $Na_2HPO_4$, 2 mM $KH_2PO_4$) for future use.

Nanozyme Treatments on Cancer Cells:

The cell line chosen for testing the c-MET nanozyme was a pancreatic cancer cell line isolated from a patient in University of Florida Health Shands Hospital (LM1). The testing details were as follows, LM1 cells were seeded in 24-well plate overnight ($1 \times 10^5$ cells per well), on the following day (day 1), old medium was removed and fresh medium (Dulbecco's Modified Eagle Medium with 10% fetal bovim serum) containing 0.5 nM Au-Rnase A, Au-Probe DNA, MET NZ and HCV NZ was added. On day 3, the old medium was removed again, and fresh medium containing 0.5 nM Au-Rnase A, Au-Probe DNA, MET NZ and HCV NZ was added. Cells were harvested on day 6 for analysis. Control cells were treated with PBS (137 mM NaCl, 2.7 mM KCl, 10 mM $Na_2HPO_4$, 2 mM $KH_2PO_4$) in the exact same way described above.

Figure 9A:
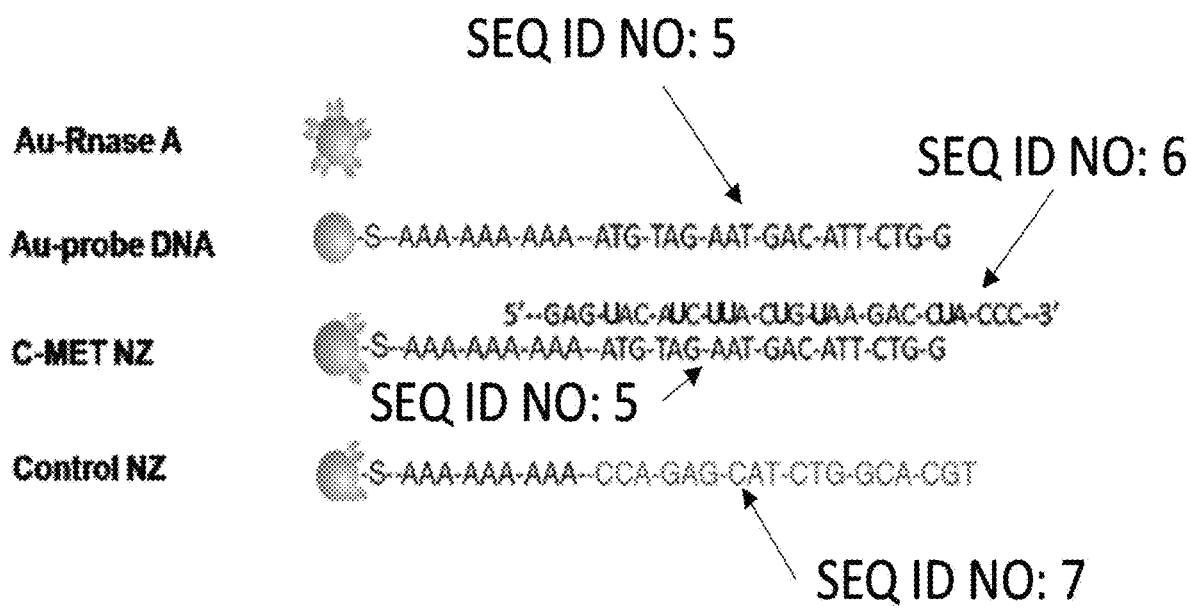
FIGS. 9A-9B demonstrate the effect of the anti c-MET nanozyme on C-MET mRNA expression.
Figure 9B:
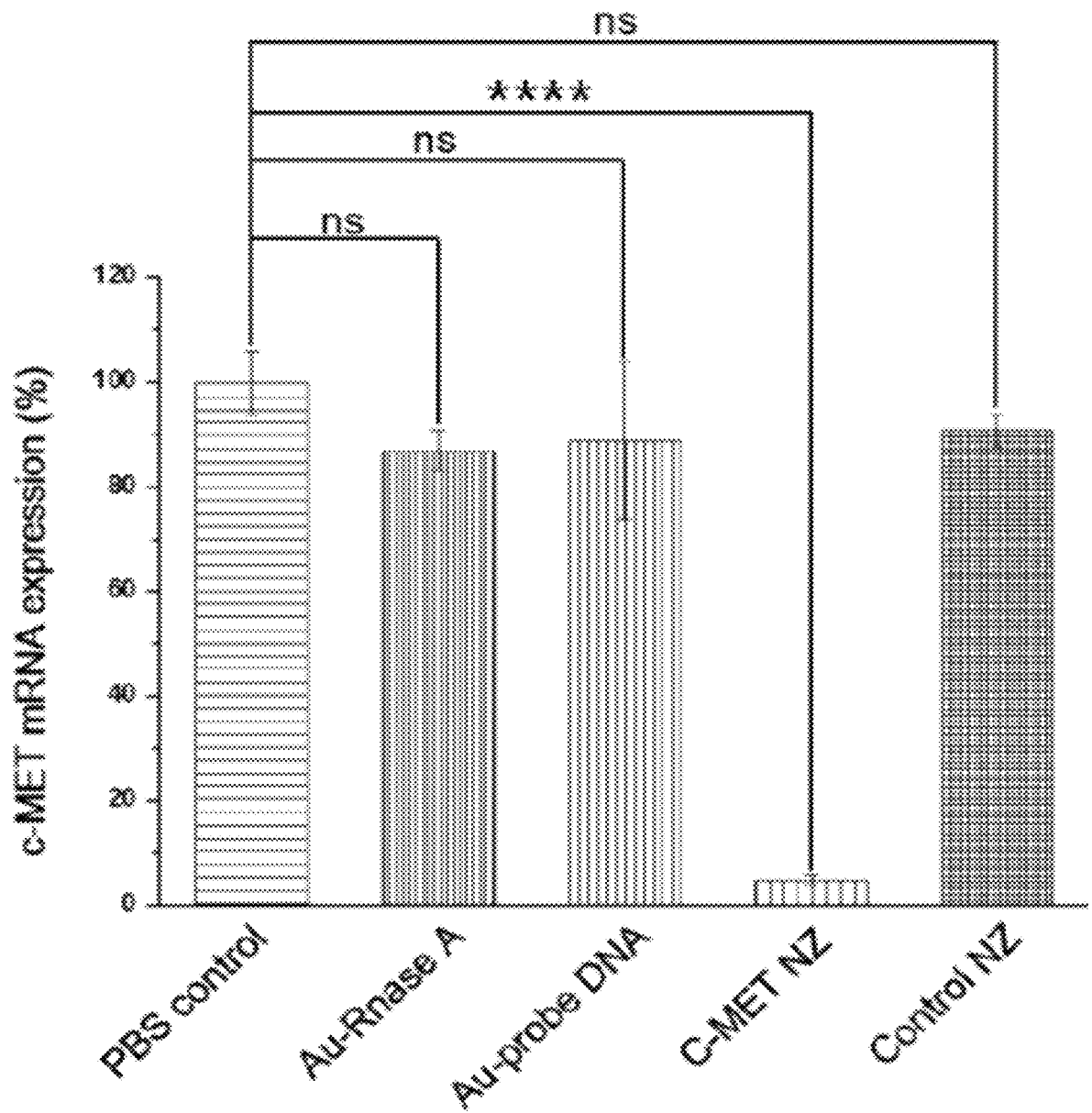

Quantitative Real Time PCR (qRT-PCR) Analysis:

Analysis of NZs' effect against target mRNA transcription was evaluated with qRT-PCR. Then total RNA was extracted from cells using TRIzol reagent following manufacturer's instructions and 2 μg total RNA were reversely transcribed into cDNAs by RT II reverse transcriptase. The obtained cDNA was used as the templates in qRT-PCR. The conditions for qRT-PCR were as follows, forward (FP) 5'-CAT-GCCGACAAGTGCAGTA-3' (SEQ ID NO: 8), reverse (RP) 5'-TCTTGCCATCATTGTCCAAC-3' (SEQ ID NO: 9). The amplification reactions were performed using Taq-Man RT-PCR on a StepOne Plus real-time PCR system (Applied Biosystems). The human GAPDH was used as an internal control in PCR amplification, and its primers were 5'-TCACCAGGGCTGCTTTTA-3' (FP) (SEQ ID NO: 10) and 5'-TTCACACCCATGACGAACA-3' (SEQ ID NO: 11) (RP). The PCR conditions were as follows: 6.25 min at 95° C. and 40 cycles of 15 s at 95° C., 30 s at 55° C. 15 seconds at 72° C., with an extension for 10 min at 60° C. The PCR results (FIGS. 9A-9B) demonstrate that the c-MET nanozyme decreased the c-MET mRNA expression in 95%. In comparison, all the other control nanozymes did not show significant effect. Au-Rnase A showed 14% decrease, Au-probe DNA showed 12% decrease and HCV NZ showed 11% decrease. All together, these results demonstrate that the c-MET nanozyme specifically effects c-MET mRNA expression.

Figure 10:
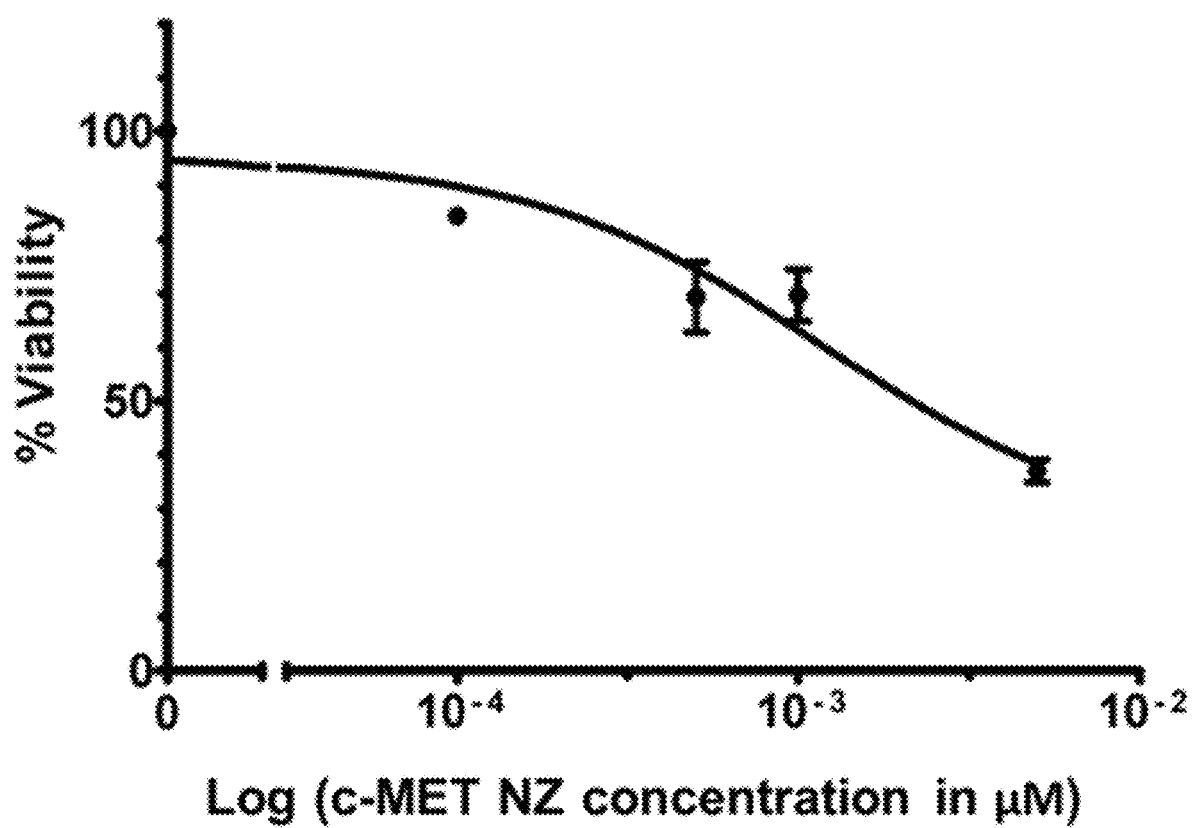
FIG. 10 shows a graph demonstrating the viability of LM1 cells treated with PBS (1×), and c-MET NZ at concentrations of 0.1 nM, 0.5 nM, 1 nM and 5 nM. Viability was presented as the percentage viability of PBS control.

Cytotoxicity Test of c-MET Nanozyme:

Cytotoxicity was evaluated using a Dojindo cell counting kit-8 assay from Dojindo molecular technologies. The cells were cultured and treated with nanozyme of 0.1 nM, 0.5 nM, 1 nM and 5 nM in the exact same way as it was in the previous test of nanozymes' activity toward the c-MET mRNA. After 6 days culturing, 50 μL cell counting kit-8 reagent was added into the medium and incubated in a $CO_2$ incubator for 4 h, then the absorbance at 450 nm was measured. The absorbance at 450 nm was directly correlated to the living cell density, the higher the living cell density, the higher the absorbance. The absorbance of cells treated with varied concentration of nanozymes were compared with the absorbance of cells treated with PBS to obtain the cell viability (FIG. 10). When treated with c-MET nanozyme (0.1 nM, 0.5 nM and 1 nM), Cells exhibited 86% 75% and 74% viability, indicating the low cytotoxity of c-MET nanozyme toward LM1 cell line. Based on the previous experiment, cells treated with 0.5 nM c-MET nanozyme already showed 95% decrease in c-MET mRNA expression. Accordingly, although the cell viability decreased to 45% when the nanozyme concentration further increase to 5 nM, under nanozymes' effective concentration toward c-MET mRNA cleavage (0.5 nM), they showed low cytotoxicity.

Example 6: Anti-EBOV Nanozymes

Establishment of a "Safe and Convenient" Ebola Replicon Model:

Ebola virus (EBOV) epidemically spreads in central Africa for almost forty years[8]. After the largest outbreak of Ebola in western Africa during 2013-2015, EBOV has already claimed 14,715 laboratory-confirmed cases and total 10,326 deaths, including sporadic cases outside of Africa in Spain, United States, and United Kingdom (CDC, Ebola Case Counts, Mar. 22, 2015), and has become an unprecedentedly public health emergency of global concern[9]. No commercially prophylactic vaccine and therapeutic regimen against EBOV, plus extreme transmissibility, EBOV has been classified as a category A pathogen that could be misused as a bioterrorism agent. Thus, there is an urgent need to develop effective therapeutic treatment for EBOV infection.

EBOV has a non-segmented, negatively single-stranded RNA molecule of approximately 19 kilobases, which codes seven proteins, including NP, VP35, VP40, GP, VP30, VP24 and L. The viral polymerase transcribes negative RNA into positive mRNA and replicates positive mRNA to synthesize the viral progeny genome and viral proteins. As of a RNA virus, analysis of full-length EBOVs sequence including human-to-human transmission viral samples shows that EBOVs undergo only limited genetic changes[10]. In addition, overall genetic variation among all EBOV genotypes remains low[11]. This novel finding is of particular importance for outbreak alert & response, public health decisions and development of novel treatment strategy. Based on the current released EBOV nucleotide sequences, 439-629 nt of GP gene (Zaire EBOV, GenBank: KP728283) is highly conserved cross all EBOVs without genetic variation. Thus, this conserved GP gene region should be an ideal target for developing interference-mediated therapy against EBOV. However, EBOV has to be performed in biosafety level (BSL)-4 laboratories. EBOV related research is very inconvenience or not accessible to researchers with regular experimental settings.

With regard to the biosafety of directly operating EBOV and the feature of autonomous replication of HCV genomic RNA, here we have designed a new EBOV model, which is based on a hybrid HCV replicon RNA. Significantly, this model can be handled in (BSL)-2 laboratories, which is widely accessible to majority of researchers. This RNA harbors a conserved EBOV genome fragment and could, in principle, replicate autonomously in cultured cells.

Figure 11:
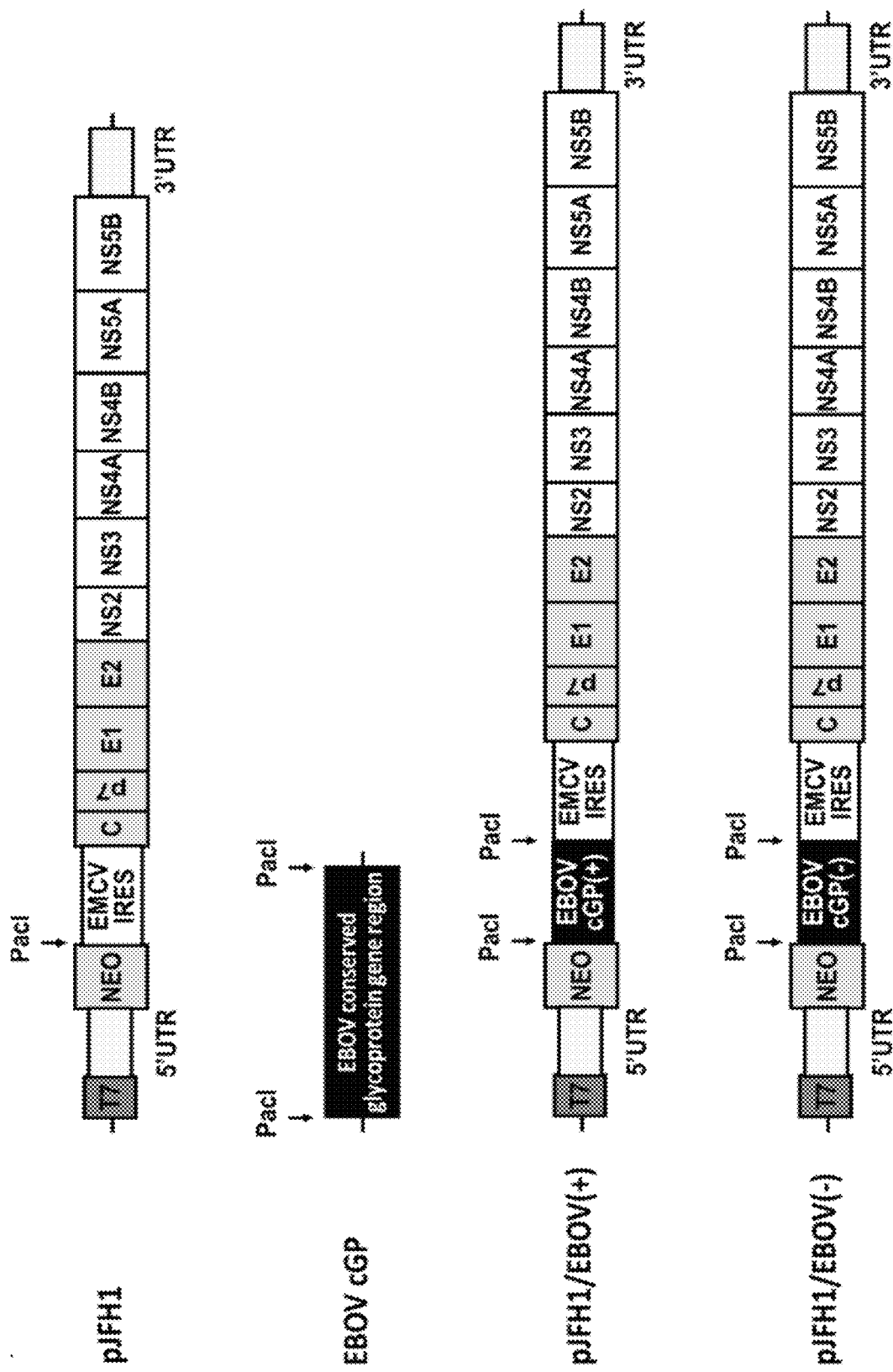
FIG. 11 shows a schematic and construction of JFH1/EBOV hybrid replicons. pJHF1 is the full length genomic replicon of HCV JFH1 strain. T7, T7 promoter. 5' UTR and 3' UTR, non-translation regions of hepatitis c virus (HCV). NEO, neomycin phosphotransferase gene. EMCV IRES, encephalomyocarditis virus internal ribosomal entry site. C, P7, E1 and E2, the structural proteins of HCV. NS2, NS3, NS4A, NS4B, NS5A and NS5B, the nonstructural proteins of HCV. EBOV cGP (−) and (+), negative strand and positive strand of Ebola virus (EBOV) conserved glycoprotein gene region locates in the 439-629 nt of glycoprotein gene (Zaire EBOV, GenBank: KP728283), which is highly conserved cross all EBOV strains. The EBOV cGP was synthesized and flanked by restriction enzyme PacI and then inserted into pJFH1 plasmid via PacI.

In this Example a synthesized self-replicating HCV/EBOV hybrid replicon RNA, which can mimic EBOV replication in vivo was used for investigating the efficacy of the anti-EBOV nanozyme against EBOV. The highly conserved EBOV 201 bp fragment of EBOV GP (EBOV cGP) was synthesized and flanked by restriction enzyme PacI. The synthesized EBOV cGP was then inserted into HCV JFH1 full-length replicon plasmid pJFH1 via PacI[13]. After transformation of One Shot® TOP10 Electrocomp™ E. coli competent bacteria (Fisher Scientific), the hybrid plasmid pJFH1/EBOV was screened by PCR with primers (Forward: CTGACCGCTTCCTCGTGCTTTAC (SEQ ID NO: 12), Reverse: GCGGCTTCGGCCAGTAAC (SEQ ID NO: 13). The positive recombinant constructs were sequenced by Interdisciplinary Center for Biotechnology Research, University of Florida. The pJFH1/EBOV (−) and pJFH1/EBOV (+) harboring negative strand EBOV cGP and positive strand EBOV cGP were confirmed by sequencing results (FIG. 11).

To examine the replication capability of hybrid replicon RNA JFH1/EBOV (−) and JFH1/EBOV (+), five microgram of hybrid plasmids pJFH1/EBOV(−), pJFH1/EBOV(+), including the control plasmid pJFH1 were linearized by restriction enzyme XbaI. The linearized hybrid plasmids were purified by gel extraction and used as template to transcribe hybrid RNA JFH1/EBOV(−) and JFH1/EBOV(+) with a MEGAscript T7 kit (Life technologies). Two hundred microliter of Huh7.5 cells with a density of 1×10⁷ cells/ml in phosphate-buffered saline (PBS) were electroporated with 5 μg transcribed hybrid RNA JFH1/EBOV(+), JFH1/EBOV (−) and JFH1 via Gene Pulser MXcell Electroporation System (Bio-Rad) at 1000 voltage, 200Ω and 25 μF. The cells were cultured in DMEM with 10% fetal bovine serum (FBS), 0.5 mg/ml G418 for 2 weeks.

Figures 12A, 12B, 12C:
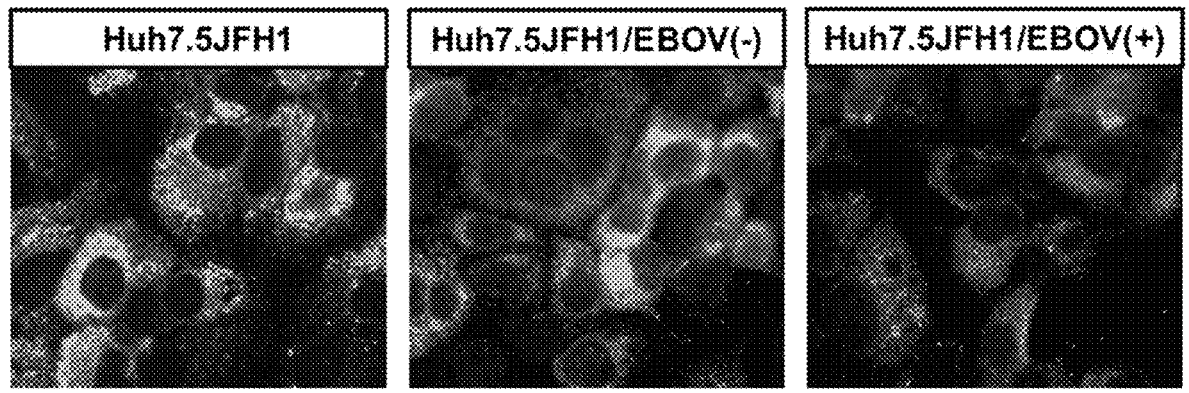
FIGS. 12A-12C show fluorescent micrographic images of pooled clones Huh7.5JFH1 (FIG. 12A), Huh7.5JFH1/EBOV(−) (FIG. 12B), and Huh7.5JFH1/EBOV(+) (FIG. 12C) after probing with an anti-HCV monoclonal antibody (mAb-HL1126 against HCV NS5A) and a fluorescently labeled secondary antibody emitting at 488 nm.

The selected clones were pooled and seeded on cover glasses in 24 well plates at a density of 5×10⁵ cells/well. Twenty-four hours later, the cover glasses were fixed with 4% paraformaldehyde and then probed with a monoclonal antibody (HL1126) against HCV NS5A for 1 hour[14]. After washing three times with PBS, the cover glasses were incubated with Alexa Fluor® 488 conjugated goat anti-mouse IgG (Life Technologies, 10 μg/ml) for 45 minutes. The pictures were taken with an Olympus BX51 microscope. As shown in FIGS. 12A-12C, the hybrid replicon exhibits robust autonomously replication ability, which is comparable to HCV control full-length replicon JFH1 RNA.

Figure 13:
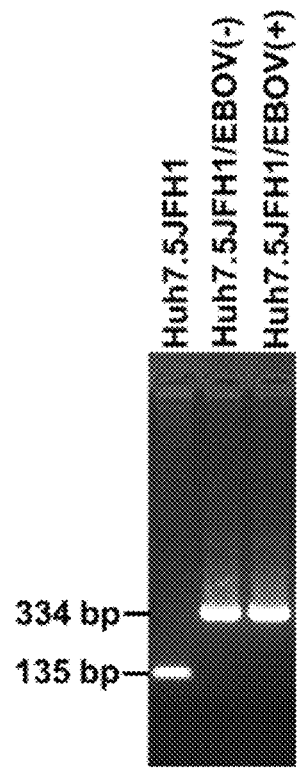
FIG. 13 shows an image demonstrating RT-PCR amplification fragments generated from JFH1/EBOV cGP (−) and JFH1/EBOV cGP (+) replicon cell lines. Insertion of EBOV cGP (−) and cGP (+) into hybrid JFH1/EBOV replicon was confirmed by RT-PCR with primers flanking cPG region in hybrid replicon. The PCR products were sequenced for the direction of cGP in hybrid replicon. The control replicon cells JFH1 only resulted in a smaller size of PCR fragment, 135 bp.
Figure 14A:
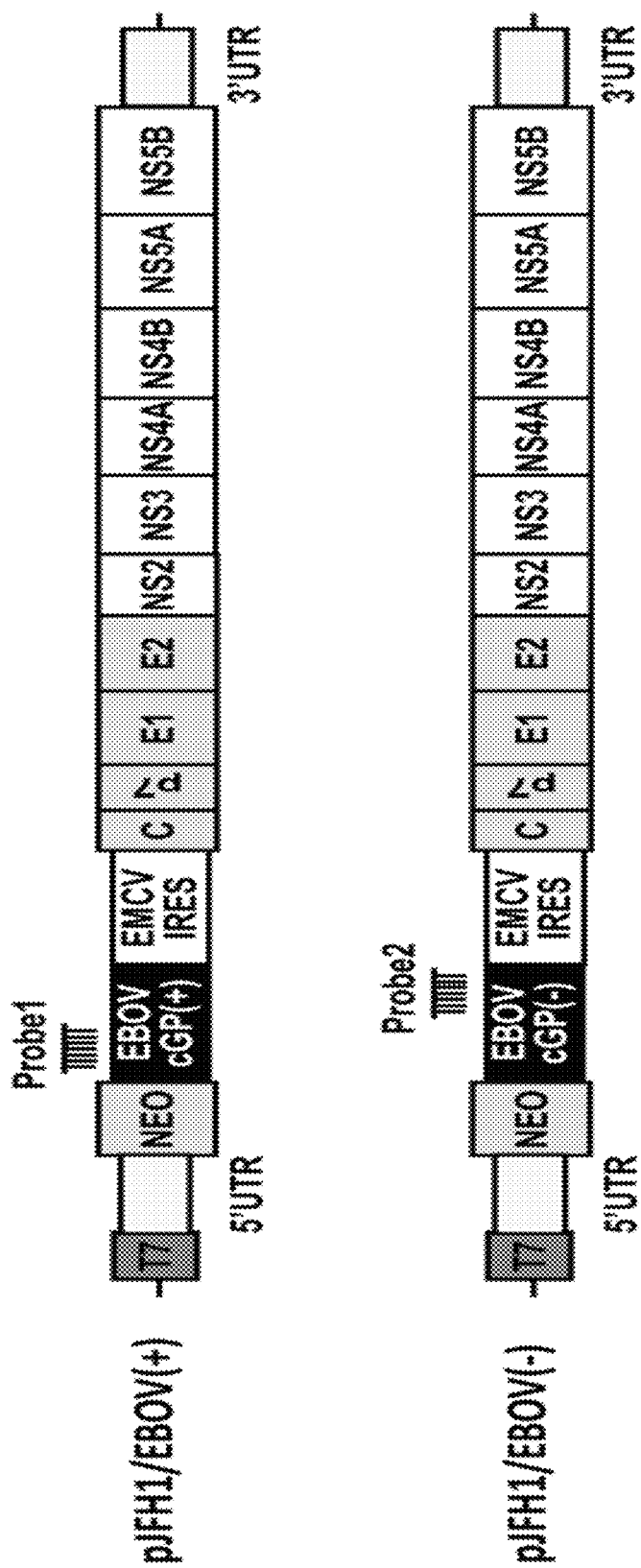

RNA was then isolated from these replicon cells using Trizol (Life Technology). One microgram of isolated RNA was subject to reverse transcription via SuperScript VILO Master Mix in 10 μl reaction system (Thermo Fisher Scientific). The cDNA was used to amplify the EBOV cGP by PCR using primers flanking cPG region (Forward: CTGAC-CGCTTCCTCGTGCTTTAC (SEQ ID NO: 14), Reverse: GCGGCTTCGGCCAGTAAC (SEQ ID NO: 15). As shown in FIG. 13, a 334 bp fragment was successfully amplified from JFH1/EBOV cGP (−) and JFH1/EBOV cGP (+) replicon cell lines. The control replicon cells JFH1 only resulted in a smaller size of PCR fragment, 135 bp.

Taken together, the immunostaining assay and PCR data demonstrate that EBOV cGP (−) and cGP (+) were inserted into hybrid replicon JFH1/EBOV and the hybrid replicon RNA is active and effectively replicating in Huh7.5 cells.

Design and Synthesis of Anti-EBOV Nanozymes:

EBOV is a negative RNA virus. After entry the host cells, negative EBOV RNA is converted to a positive RNA by RNA polymerase before translation[15]. The positive strand RNA acts as mRNA to translate viral protein. For production of newly assembled EBOV, more negative sense RNA molecules are needed. The positive strand EBOV RNA functions as template to make negative RNA strands. In order to make our novel anti-viral nanozyme much more robust, here we designed two different probe targets. Probe 1 targets the positive strand EBOV RNA and probe 2 targets the negative strand EBOV RNA. These two probes will synergistically disable the negative and positive strands EBOV RNA, which are essential for viral replication and virions production. Probe sequences were selective by GC % and melting temperature. The ideal probe sequences are GC % close to 50% and melting temperature is close 50° C. Probe 1 was designed to bind a target on the positive Ebola strand: (5' GTGGAAGCAAGTCGATCA 3') (SEQ ID NO: 16) and Probe 2 was designed to bind a target on the negative Ebola strand (5' CTACCGAGGAACGACTTT 3') (SEQ ID NO: 17), which have the high scores based on the selection standard (FIGS. 11A-11B). To make the corresponding probes, 9 A nucleotides were added to the 3' end of the Ebola target sequences, similar to the c-MET probe of Example 5: Probe 1 5' GTGGAAGCAAGTCGATCAAAAAAAAAA 3' (SEQ ID NO: 18) and Probe 2: 5' CTACCGAGGAAC-GACTTT AAAAAAAAA 3' (SEQ ID NO: 19).

For the synthesis of anti-EBOV nanozymes, 10 nM of Au NPs can be mixed by shaking with 0.5 μM Rnase A (2 mL, 1.3 mM Na2CO3 pH 9.8) for 30 min at room temperature. Then 6.4 nmol probe DNA can be added in and the solution is proposed to be turned into 10 mM phosphate pH 7.4. After 8 h shaking under room temperature, NaCl (1.5 M) is proposed to be added in to gradually bring the NaCl concentration to 0.3 M in 32 h. The solution can be further shaken for 8 h. The NZs can then be purified by centrifuge (13,000 rpm, 30 min 3 times) and redispersed in PBS for future use.

Anti EBOV Effects of Nanozyme in Cultured Cells:

To evaluate the antiviral effects of our novel anti-EBOV nanozymes in cultured replicon cells, the hybrid replicon cells Huh7.5JFH1/EBOV (−) and Huh7.5 JFH1/EBOV (+) were seeded on cover glassed in 24 well plates at a density of 1×105 cells/well. Twenty-four hour later, the anti-EBOV nanozymes (probe 1 and probe 2) and control nanoparticles were added in 5 nM with every 2 days.

Six days later, the cover glasses were fixed with 4% paraformaldehyde and then probed with monoclonal antibody (HL1126) against HCV NS5A for 1 hour. After three times wash with PBS, the cover glasses were incubated with Alexa Fluor® 488 conjugated goat anti-mouse IgG (Life Technologies, 10 μg/ml) for 45 minutes. The pictures were taken with an Olympus BX51 microscope and analyzed by ImageJ. The percentage and extensive fluorescence is positive related to the replication level of hybrid RNA JFH1/EBOV(−) and JFH1/EBOV(+). As shown in FIGS. 15A-15D, anti-EBOV nanozyme reduced the replication level of HCV JFH1/EBOV hybrid replicon to more than 90%. DNA probe 1 targeting positive strand of EBOV RNA (FIG. 15A) has much more effects than the probe 2 targeting negative strand of EBOV RNA (FIG. 15B). Relative RNA replication level is normalized to control group (FIG. 15C and FIG. 15D).

The immunostaining assay results demonstrates that both anti-EBOV nanozymes with DNA probes targeting negative and positive strand EBOV RNA exhibit effects in restricting the replication of hybrid HCV/EBOV replicon RNA in culture cells.

REFERENCES FOR EXAMPLES 5 AND 6

1. Farazi, P. A. & DePinho, R. A. Hepatocellular carcinoma pathogenesis: from genes to environment. *Nat Rev Cancer* 6, 674-87 (2006).
2. El-Serag, H. B. Hepatocellular carcinoma. *N Engl J Med* 365, 1118-27 (2011).
3. Scagliotti, G. V., Novello, S. & von Pawel, J. The emerging role of MET/HGF inhibitors in oncology. *Cancer treatment reviews* 39, 793-801 (2013).
4. Venepalli, N. K. & Goff, L. Targeting the HGF-cMET Axis in Hepatocellular Carcinoma. *Int J Hepatol* 2013, 1-11 (2013).
5. Yap, T. A. & de Bono, J. S. Targeting the HGF/c-Met axis: state of play. Mol Cancer Ther 9, 1077-9 (2010).
6. Cecchi, F., Rabe, D. C. & Bottaro, D. P. Targeting the HGF/Met signalling pathway in cancer. *Eur J Cancer* 46, 1260-70 (2010).
7. Wang, Z. L., Liu, H. Y, Yang, S. H., et al. Nanoparticle-based artificial RNA silencing machinery for antiviral therapy, *Proc. Natl. Acad. Sci.* 106, 12387-12392 (2012).
8. Dudas G, Rambaut A. Phylogenetic Analysis of Guinea 2014 EBOV Ebolavirus Outbreak. PLoS Curr 2014; 6.

9. Team WHOER. Ebola virus disease in West Africa—the first 9 months of the epidemic and forward projections. N Engl J Med 2014; 371:1481-95.
10. Hoenen T, Safronetz D, Groseth A, et al. Virology. Mutation rate and genotype variation of Ebola virus from Mali case sequences. Science 2015; 348:117-9.
11. Rodriguez L L, De Roo A, Guimard Y, et al. Persistence and genetic stability of Ebola virus during the outbreak in Kikwit, Democratic Republic of the Congo, 1995. J Infect Dis 1999; 179 Suppl 1:S170-6.
13. Date T, Miyamoto M, Kato T, et al. An infectious and selectable full-length replicon system with hepatitis C virus JFH-1 strain. Hepatol Res 2007; 37:433-43.
14. Yang D, Zuo C, Wang X, et al. Complete replication of hepatitis B virus and hepatitis C virus in a newly developed hepatoma cell line. Proc Natl Acad Sci USA 2014; 111:E1264-73.
15. Palese P, Zheng H, Engelhardt O G, et al. Negative-strand RNA viruses: genetic engineering and applications. Proc Natl Acad Sci USA 1996; 93:11354-8.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A nanozyme comprising:
a shell surrounding a hollow core configured to receive a compound, wherein the shell comprises:
a single stranded DNA (ssDNA) recognition moiety selected from the group consisting of: a polynucleotide set forth in SEQ ID NO: 1, SEQ ID NO: 2, SEQ ID NO: 3, SEQ ID NO: 4, SEQ ID NO: 5, SEQ ID NO: 16, SEQ ID NO: 17, and combinations thereof,
wherein the ssDNA recognition moiety comprises an alkylthiol-terminated propargyl ether modified poly-thymine polynucleotide; wherein the alkylthiol-terminated, propargyl ether modified poly-thymine polynucleotide comprises one or more propargyl ether groups coupled via an amidohexylacrylamido linker to the 5' position of one or more thymine bases, and wherein the ssDNA recognition moiety specifically binds, through reverse complementary binding, a polynucleotide selected from the group consisting of: a c-MET mRNA, a conserved Glycoprotein (cGP) region of a positive RNA strand of Ebola virus, a cGP region of a negative RNA strand of Ebola virus, a survivin mRNA, and a bcl 2 mRNA, and
an endoribonuclease-oligonucleotide complex comprising an endoribonuclease coupled to an alkylthiol-terminated, propargyl ether modified poly-thymine polynucleotide, wherein the alkylthiol-terminated, propargyl ether modified poly-thymine polynucleotide comprises one or more propargyl ether groups coupled via an amidohexylacrylamido linker to the 5' position of one or more thymine bases, and
wherein at least some of the propargyl ether groups on the alkylthiol-terminated propargyl ether modified poly-thymine polynucleotide of the endoribonuclease-oligonucleotide complex, of the ssDNA recognition moiety, or of the endoribonuclease-oligonucleotide complex and the ssDNA recognition moiety are crosslinked.

2. The nanozyme of claim 1, wherein the shell further comprises a block copolymer comprising polyethylene glycol and lysine.

3. The nanozyme of claim 2, wherein the block copolymer is methoxy-PEG-block-poly(L-lysine) hydrobromide.

4. The nanozyme of claim 1, wherein the shell is substantially solid.

5. The nanozyme of claim 1, wherein the shell is porous.

6. The nanozyme of claim 1, further comprising a protecting moiety, wherein the protecting moiety is attached to the shell of the nanozyme, and
wherein the protecting moiety is selected from the group consisting of: a DNA oligonucleotide, a locked nucleic acid, a peptide nucleic acid, a poly(ethylene glycol), a poly(vinyl alcohol), a poly(acrylic acid), a poly(propylene fumarate-co-ethylene glycol), a polyacrylamide, a polypeptide, a poly-N-substituted glycine oligomer, a hyaluronic acid, an alginate, a chitosan, an agarose, a collagen, a fibrin, a gelatin, a dextran, and any combination thereof.

7. The nanozyme of claim 1, further comprising an intra- or inter-cellular traffic guiding moiety, wherein the intra- or inter-cellular traffic guiding moiety is attached to the shell of the nanozyme.

8. The nanozyme of claim 1, further comprising an allosterically functional moiety, wherein the allosterically functional moiety is attached to the shell of the nanozyme.

9. The nanozyme of claim 1, wherein the shell further comprises a polymer layer, wherein the polymer layer is attached to the recognition moiety, the enzyme or both the recognition moiety and the enzyme.

10. The nanozyme of claim 9, wherein the polymer layer comprises a plurality of pores.

11. The nanozyme of claim 9, wherein the polymer layer consists of a polymer selected from the group consisting of: of a polyalkyne, a polyolefin, a polyisoprene, a polyamide, a polyester, a polycarbonate, a silicone, co-polymers thereof, and combinations thereof.

12. The nanozyme of claim 1, further comprising an active agent, wherein the agent is contained in the hollow core.

13. The nanozyme of claim 12, wherein the agent is a therapeutic agent.

14. The nanozyme of claim 13, wherein the agent is selected from the group consisting of: a small molecule, a peptide, a nucleic acid, a polymer, and combinations thereof.

15. The nanozyme of claim 1, wherein the agent is an imaging agent.

16. The nanozyme of claim 15, wherein the imaging agent is selected from the group consisting of: a dye, a metal oxide nanoparticle, a metal nanoparticle, a semiconductor ananoparticle quantum dots, and a diamond nanoparticle, and combinations thereof.

17. The nanozyme of claim 1, further comprising an imaging agent, wherein the imaging agent is attached to the shell.

18. The nanozyme of claim 17, wherein the imaging agent is selected from the group consisting of: a dye, a metal oxide nanoparticle, a metal nanoparticle, a semiconductor a nanoparticle quantum dots, and a diamond nanoparticle, and combinations thereof.

19. The nanozyme of claim 1, wherein the endoribonuclease is selected from the group consisting of: RNA RNase A, RNase III, RNase H, RNase P, RNase T1, and combinations thereof.

20. A pharmaceutical formulation comprising:
a nanozyme, wherein the nanozyme comprises:
    a shell surrounding a hollow core configured to receive a compound, wherein the shell comprises:
        a single stranded DNA (ssDNA) recognition moiety selected from the group consisting of: a polynucleotide set forth in SEQ ID NO: 1, SEQ ID NO: 2, SEQ ID NO: 3, SEQ ID NO: 4, SEQ ID NO: 5, SEQ ID NO: 16, SEQ ID NO: 17, and combinations thereof, wherein the ssDNA recognition moiety comprises an alkylthiol-terminated propargyl ether modified poly-thymine polynucleotide; wherein the alkylthiol-terminated, propargyl ether modified poly-thymine polynucleotide comprises one or more propargyl ether groups coupled via an amidohexylacrylamido linker to the 5' position of one or more thymine bases, and wherein the ssDNA recognition moiety specifically binds, through reverse complementary binding, a polynucleotide selected from the group consisting of: a c-MET mRNA, a conserved Glycoprotein (cGP) region of a positive RNA strand of Ebola virus, a cGP region of a negative RNA strand of Ebola virus, a survivin mRNA, and a bcl 2 mRNA;
    an endoribonuclease-oligonucleotide complex comprising an endoribonuclease coupled to an alkylthiol-terminated, propargyl ether modified poly-thymine polynucleotide, wherein the alkylthiol-terminated, propargyl ether modified poly-thymine polynucleotide comprises one or more propargyl ether groups coupled via an amidohexylacrylamido linker to the 5' position of one or more thymine bases, and
wherein at least some of the propargyl ether groups on the alkylthiol-terminated propargyl ether modified poly-thymine polynucleotide of the endoribonuclease-oligonucleotide complex, of the ssDNA recognition moiety, or of the endoribonuclease-oligonucleotide complex and the ssDNA recognition moiety are crosslinked; and
a pharmaceutically acceptable carrier.

21. A method comprising:
administering a nanozyme to a subject, wherein the nanozyme comprises a shell surrounding a hollow core configured to receive a compound, wherein the shell comprises:
a single stranded DNA (ssDNA) recognition moiety selected from the group consisting of: a polynucleotide set forth in SEQ ID NO: 1, SEQ ID NO: 2, SEQ ID NO: 3, SEQ ID NO: 4, SEQ ID NO: 5, SEQ ID NO: 16, SEQ ID NO: 17, and combinations thereof, wherein the ssDNA recognition moiety is functionalized with comprises an alkylthiol-terminated propargyl ether modified poly-thymine polynucleotide; wherein the alkylthiol-terminated, propargyl ether modified poly-thymine polynucleotide comprises one or more propargyl ether groups coupled via an amidohexylacrylamido linker to the 5' position of one or more thymine bases, and wherein the ssDNA recognition moiety specifically binds, through reverse complementary binding, a polynucleotide selected from the group consisting of: a c-MET mRNA, a conserved Glycoprotein (cGP) region of a positive RNA strand of Ebola virus, a cGP region of a negative RNA strand of Ebola virus, a survivin mRNA, and a bcl 2 mRNA, and an endoribonuclease-oligonucleotide complex comprising an endoribonuclease coupled to an alkylthiol-terminated, propargyl ether modified poly-thymine polynucleotide, wherein the alkylthiol-terminated, propargyl ether modified poly-thymine polynucleotide comprises one or more propargyl ether groups coupled via an amidohexylacrylamido linker to the 5' position of one or more thymine bases, and wherein at least some of the propargyl ether groups on the alkylthiol-terminated propargyl ether modified poly-thymine polynucleotide of the endoribonuclease-oligonucleotide complex, of the ssDNA recognition moiety, or of the endoribonuclease-oligonucleotide complex and the ssDNA recognition moiety are crosslinked.

22. The method of claim 21, wherein the subject has hepatitis B virus (HBV) disease, hepatitis C virus (HCV) disease, human papilloma virus (HPV) disease, hepatocellular carcinoma (HCC), ebola virus (EBOV) disease, or a liver cancer.

23. The nanozyme of claim 20, wherein the endoribonuclease is selected from the group consisting of: RNA RNase A, RNase III, RNase H, RNase P, RNase T1, and combinations thereof.

* * * * *

SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: survivin antisense sequence (1)

<400> SEQUENCE: 1
tgtagagatg cggtggtcc 19

<210> SEQ ID NO 2
<211> LENGTH: 19
<212> TYPE: DNA
<213> ORGANISM: Artificial Sequence
<220> FEATURE:
<223> OTHER INFORMATION: survivin antisense sequence 2

<400> SEQUENCE: 2
gatggcacgg cgcactttc 19

<210> SEQ ID NO 3
<211> LENGTH: 22
<212> TYPE: DNA
<213> ORGANISM: Artificial Sequence
<220> FEATURE:
<223> OTHER INFORMATION: bcl 2 antisense sequence (1)

<400> SEQUENCE: 3
ggtctgcagc ggcgaggtcc tg 22

<210> SEQ ID NO 4
<211> LENGTH: 21
<212> TYPE: DNA
<213> ORGANISM: Artificial Sequence
<220> FEATURE:
<223> OTHER INFORMATION: bcl 2 antisense sequence (2)

<400> SEQUENCE: 4

```
gtctgcagcg gcgaggtcct g                                              21

<210> SEQ ID NO 5
<211> LENGTH: 28
<212> TYPE: DNA
<213> ORGANISM: Artificial Sequence
<220> FEATURE:
<223> OTHER INFORMATION: c-MET probe

<400> SEQUENCE: 5
ggtcttacag taagatgtaa aaaaaaaa                                       28

<210> SEQ ID NO 6
<211> LENGTH: 27
<212> TYPE: DNA
<213> ORGANISM: Artificial Sequence
<220> FEATURE:
<223> OTHER INFORMATION: c-MET probe target sequence

<400> SEQUENCE: 6
gaguacaucu uacuguaaga ccuaccc                                        27

<210> SEQ ID NO 7
<211> LENGTH: 27
<212> TYPE: DNA
<213> ORGANISM: Artificial Sequence
<220> FEATURE:
<223> OTHER INFORMATION: Control NZ probe sequence

<400> SEQUENCE: 7
aaaaaaaaac cagagcatct ggcacgt                                        27

<210> SEQ ID NO 8
<211> LENGTH: 19
<212> TYPE: DNA
<213> ORGANISM: Artificial Sequence
<220> FEATURE:
<223> OTHER INFORMATION: forward qRT-PCR primer

<400> SEQUENCE: 8
catgccgaca agtgcagta                                                 19

<210> SEQ ID NO 9
<211> LENGTH: 20
<212> TYPE: DNA
<213> ORGANISM: Artificial Sequence
<220> FEATURE:
<223> OTHER INFORMATION: reverse qRT-PCR primer

<400> SEQUENCE: 9
tcttgccatc attgtccaac                                                20

<210> SEQ ID NO 10
<211> LENGTH: 18
<212> TYPE: DNA
<213> ORGANISM: Artificial Sequence
<220> FEATURE:
<223> OTHER INFORMATION: forward human GAPDH qRT-PCR primer

<400> SEQUENCE: 10
tcaccagggc tgcttttta                                                 18

<210> SEQ ID NO 11
<211> LENGTH: 19
<212> TYPE: DNA
<213> ORGANISM: Artificial Sequence
```

```
<220> FEATURE:
<223> OTHER INFORMATION: reverse human GAPDH qRT-PCR primer

<400> SEQUENCE: 11
ttcacaccca tgacgaaca                                                      19

<210> SEQ ID NO 12
<211> LENGTH: 23
<212> TYPE: DNA
<213> ORGANISM: Artificial Sequence
<220> FEATURE:
<223> OTHER INFORMATION: forward pJFH1/EBOV PCR primer

<400> SEQUENCE: 12
ctgaccgctt cctcgtgctt tac                                                 23

<210> SEQ ID NO 13
<211> LENGTH: 18
<212> TYPE: DNA
<213> ORGANISM: Artificial Sequence
<220> FEATURE:
<223> OTHER INFORMATION: reverse pJFH1/EBOV  PCR primer

<400> SEQUENCE: 13
gcggcttcgg ccagtaac                                                       18

<210> SEQ ID NO 14
<211> LENGTH: 23
<212> TYPE: DNA
<213> ORGANISM: Artificial Sequence
<220> FEATURE:
<223> OTHER INFORMATION: forward EBOV cGP PCR primer

<400> SEQUENCE: 14
ctgaccgctt cctcgtgctt tac                                                 23

<210> SEQ ID NO 15
<211> LENGTH: 18
<212> TYPE: DNA
<213> ORGANISM: Artificial Sequence
<220> FEATURE:
<223> OTHER INFORMATION: reverse EBOV cGP PCR primer

<400> SEQUENCE: 15
gcggcttcgg ccagtaac                                                       18

<210> SEQ ID NO 16
<211> LENGTH: 18
<212> TYPE: DNA
<213> ORGANISM: Artificial Sequence
<220> FEATURE:
<223> OTHER INFORMATION: Ebola Positive strand nanozyme target

<400> SEQUENCE: 16
gtggaagcaa gtcgatca                                                       18

<210> SEQ ID NO 17
<211> LENGTH: 18
<212> TYPE: DNA
<213> ORGANISM: Artificial Sequence
<220> FEATURE:
<223> OTHER INFORMATION: Ebola negative strand nanozyme target

<400> SEQUENCE: 17
ctaccgagga acgacttt                                                       18
```

-continued

```
<210> SEQ ID NO 18
<211> LENGTH: 26
<212> TYPE: DNA
<213> ORGANISM: Artificial Sequence
<220> FEATURE:
<223> OTHER INFORMATION: Ebola nanozyme probe sequence

<400> SEQUENCE: 18
tggaagcaag tcgatcaaaa aaaaaa                                            26

<210> SEQ ID NO 19
<211> LENGTH: 27
<212> TYPE: DNA
<213> ORGANISM: Artificial Sequence
<220> FEATURE:
<223> OTHER INFORMATION: Ebola nanozyme probe sequence

<400> SEQUENCE: 19
ctaccgagga acgactttaa aaaaaaa                                           27
```